United States Patent
Kitta et al.

(10) Patent No.: US 8,865,433 B2
(45) Date of Patent: Oct. 21, 2014

(54) METHOD FOR QUALITATIVE AND QUANTITATIVE DETECTION OF COMMON WHEAT

(75) Inventors: Kazumi Kitta, Tsukuba (JP); Satoshi Furui, Tsukuba (JP); Junichi Mano, Tsukuba (JP); Yasuyuki Matsuoka, Atsugi (JP); Shinichiro Arami, Atsugi (JP); Megumi Sato, Atsugi (JP); Hiroyuki Haraguchi, Atsugi (JP); Youichi Kurimoto, Atsugi (JP); Shinjiro Imai, Fujimino (JP); Keiko Tanaka, Fujimino (JP)

(73) Assignees: Nippon Flour Mills Co., Ltd, Tokyo (JP); Nisshin Seifun Group Inc, Tokyo (JP)

( * ) Notice: Subject to any disclaimer, the term of this patent is extended or adjusted under 35 U.S.C. 154(b) by 342 days.

(21) Appl. No.: 13/518,298

(22) PCT Filed: Dec. 17, 2010

(86) PCT No.: PCT/JP2010/072806
§ 371 (c)(1),
(2), (4) Date: Jun. 21, 2012

(87) PCT Pub. No.: WO2011/078093
PCT Pub. Date: Jun. 30, 2011

(65) Prior Publication Data
US 2012/0264128 A1 Oct. 18, 2012

(30) Foreign Application Priority Data
Dec. 21, 2009 (JP) ................... 2009-289340

(51) Int. Cl.
*C12P 19/34* (2006.01)
*C12Q 1/68* (2006.01)

(52) U.S. Cl.
CPC .................. *C12Q 1/6895* (2013.01)
USPC ....................................................... 435/91.2

(58) Field of Classification Search
USPC ....................................................... 435/91.2
See application file for complete search history.

(56) References Cited

U.S. PATENT DOCUMENTS

| 8,053,628 | B2 | 11/2011 | Nakamura et al. |
| 2009/0285960 | A1 | 11/2009 | Nakamura et al. |
| 2010/0062432 | A1 | 3/2010 | Imai et al. |

FOREIGN PATENT DOCUMENTS

| EP | 1 878 337 A | | 1/2008 |
| JP | 2005-333832 A | | 12/2005 |
| JP | 2009-005588 A | | 1/2009 |
| WO | WO 0066745 | * | 11/2000 |
| WO | 2007/132760 A1 | | 11/2007 |

OTHER PUBLICATIONS

Vautrin and Zhang., J. AOAC Int., 90(3): 794-801, May-Jun. 2007.*
T. Shimbata, et al., "Mutations in wheat *starch synthase II* genes and PCR-based selection of a SGP-1 null line", Theor. Appl. Genet., 2005, pp. 1072-1079, vol. 111.
Zhongyi Li, et al., "The Localization and Expression of the Class II Starch Synthases of Wheat", Plant Physiology, Aug. 1999, pp. 1147-1155, vol. 120.
Mayu Iida, et al., "Development of Taxon-Specific Sequences of Common Wheat for the Detection of Genetically Modified Wheat", J. Agric. Food. Chem., 2005, pp. 6294-6300, vol. 53, No. 16.
Tomoaki Yoshimura, et al., "Comparative Studies of the Quantification of Genetically Modified Organisms in Foods Processed from Maize and Soy Using Trial Producing", J. Agric. Food. Chem., 2005, pp. 2060-2069, vol. 53, No. 6.
Matsuoka et al., "Development of Methods to Distinguish between Durum/Common Wheat and Common Wheat in Blended Flour Using PCR," Food Hyg. Saf. Sci., 2012, vol. 53, pp. 195-202.
European Patent Office, European Search Report issued in corresponding EP Application No. 10839323.2, dated Jun. 25, 2013.

* cited by examiner

*Primary Examiner* — Cynthia B Wilder
(74) *Attorney, Agent, or Firm* — Sughrue Mion, PLLC

(57) ABSTRACT

Disclosed are: a method for detecting common wheat among from wheat varieties contained in a sample of interest such as a food raw material or a processed food specifically, with high sensitivity, and in a qualitative and/or quantitative manner; a method for discriminating between common wheat and a wheat variety other than common wheat (e.g., durum wheat) contained in a food raw material or a processed food and detecting the common wheat in a qualitative and/or quantitative manner; and a primer set, a nucleic acid probe, and a detection kit, each of which can be used in the methods employing a PCR method. Specifically disclosed are: a method for detecting the occurrence of common wheat in a sample of interest, which comprises carrying out a PCR method using a nucleic acid extracted from the sample as a template and using a primer comprising the nucleotide sequence represented by SEQ ID NO:5 and a primer comprising the nucleotide sequence represented by SEQ ID NO:6 and detecting the occurrence of a PCR amplification product; and a method for detecting the occurrence of common wheat in a sample of interest, which comprises carrying out a quantitative PCR method using a nucleic acid extracted from the sample as a template and using a primer comprising the nucleotide sequence represented by SEQ ID NO:5, a primer comprising the nucleotide sequence represented by SEQ ID NO:6 and a nucleic acid probe comprising the nucleotide sequence represented by SEQ ID NO:11 and detecting the occurrence of common wheat qualitatively and/or quantitatively.

7 Claims, 9 Drawing Sheets

SEQUENCE LISTING

<160> NUMBER OF SEQ ID NOS: 14

<210> SEQ ID NO 1
<211> LENGTH: 23
<212> TYPE: DNA
<213> ORGANISM: Artificial Sequence

```
<220> FEATURE:
<223> OTHER INFORMATION: PCR primer

<400> SEQUENCE: 1
caacatccgc aaatagtgag cat                                              23

<210> SEQ ID NO 2
<211> LENGTH: 21
<212> TYPE: DNA
<213> ORGANISM: Artificial Sequence
<220> FEATURE:
<223> OTHER INFORMATION: PCR primer

<400> SEQUENCE: 2
ggctaggtcg ggctctatga g                                                21

<210> SEQ ID NO 3
<211> LENGTH: 19
<212> TYPE: DNA
<213> ORGANISM: Artificial Sequence
<220> FEATURE:
<223> OTHER INFORMATION: PCR primer

<400> SEQUENCE: 3
tcctcgacct cccattcca                                                   19

<210> SEQ ID NO 4
<211> LENGTH: 25
<212> TYPE: DNA
<213> ORGANISM: Artificial Sequence
<220> FEATURE:
<223> OTHER INFORMATION: PCR primer

<400> SEQUENCE: 4
ccggtgttag ttctatgatg attcg                                            25

<210> SEQ ID NO 5
<211> LENGTH: 23
<212> TYPE: DNA
<213> ORGANISM: Artificial Sequence
<220> FEATURE:
<223> OTHER INFORMATION: PCR primer

<400> SEQUENCE: 5
caccatcagt gaaggaatga atg                                              23

<210> SEQ ID NO 6
<211> LENGTH: 25
<212> TYPE: DNA
<213> ORGANISM: Artificial Sequence
<220> FEATURE:
<223> OTHER INFORMATION: PCR primer

<400> SEQUENCE: 6
ggcgatattt ggtacctaat tgaag                                            25

<210> SEQ ID NO 7
<211> LENGTH: 19
<212> TYPE: DNA
<213> ORGANISM: Artificial Sequence
<220> FEATURE:
<223> OTHER INFORMATION: PCR primer

<400> SEQUENCE: 7
tccgttgtcc cagctgaga                                                   19
```

-continued

```
<210> SEQ ID NO 8
<211> LENGTH: 20
<212> TYPE: DNA
<213> ORGANISM: Artificial Sequence
<220> FEATURE:
<223> OTHER INFORMATION: PCR primer

<400> SEQUENCE: 8
tggctttgga gcttcttcga                                                   20

<210> SEQ ID NO 9
<211> LENGTH: 19
<212> TYPE: DNA
<213> ORGANISM: Artificial Sequence
<220> FEATURE:
<223> OTHER INFORMATION: PCR primer

<400> SEQUENCE: 9
ggatggaaat ctggtgttt                                                    19

<210> SEQ ID NO 10
<211> LENGTH: 21
<212> TYPE: DNA
<213> ORGANISM: Artificial Sequence
<220> FEATURE:
<223> OTHER INFORMATION: PCR primer

<400> SEQUENCE: 10
accataatgg accgagtgta c                                                 21

<210> SEQ ID NO 11
<211> LENGTH: 23
<212> TYPE: DNA
<213> ORGANISM: Artificial Sequence
<220> FEATURE:
<221> NAME/KEY: modified_base
<223> OTHER INFORMATION: Probe for PCR, 1-FAM-a, 23-a-TAMRA

<400> SEQUENCE: 11
tacccgatcg accgttttgc cca                                               23

<210> SEQ ID NO 12
<211> LENGTH: 7010
<212> TYPE: DNA
<213> ORGANISM: Triticum aestivum
<220> FEATURE:
<221> NAME/KEY: CDS
<222> LOCATION: join(236..499, 604..1309, 1398..1462, 2363..2440,
      2530..2640, 2738..2782, 3163..3336, 6054..7010)
<223> OTHER INFORMATION: Triticum aestivum wSSII-D gene for starch
      synthase II-D, complete cds.

<400> SEQUENCE: 12
gggggccgtt cgtacgtacc cgcccctcgt gtaaagccgc cgccgtcgtc gccgtccccc       60
gctcgcggcc atttcttcgg cctgaccccg ttcgtttacc cccacacaga gcacactcca      120
gtccagtcca gcccactgcc accgcgctac tctccactcc cactgccacc acctccgcct      180
gcgccgcgct ctgggcggac caacccgcga accgtaccat ctcccgcccc gatccatgtc      240
gtcggcggtc gcgtccgccg catccttcct cgcgctcgcg tcagcctccc ccggagatc       300 acgcaggcgg gcgagggtga gcgcgcagcc accccacgcc ggggccggca ggttgcactg      360
gccgccgtgg ccgccgcagc gcacggctcg cgacggagct gtggcggcgc tcgccgccgg      420
gaagaaggac gcgggggatcg acgacgccgc cgcgtccgtg aggcagcccc gcgcactccg      480
cggtggcgcc gccaccaagg tagttagtta tgaccaagtt atgacgcgtg cgcgcgcctc      540
```

```
gagatcatcg tcgtctcgct cacgaattgt ttatttatac aaaacgcacg cccgcgtgtg      600
caggtcgcgg agcgaaggga tcccgtcaag acgctcgacc gcgacgccgc ggaaggcggc      660
gggccgtccc cgccggcagc gaggcaggac gccgcccgtc cgccgagtat gaacggcatg      720
ccggtgaacg gcgagaacaa atctaccggc ggcggcggcg cgactaaaga cagcgggctg      780
cccacgcccg cacgcgcgcc ccatccgtcg acccagaaca gagcaccggt gaacggtgaa      840
aacaaagcta acgtcgcctc gccgccgacg agcatagccg aggccgcggc ttcggattcc      900
gcagctacca tttccatcag cgacaaggcg ccggagtccg ttgtcccagc tgagaagacg      960
ccgccgtcgt ccggctcaaa tttcgagtcc tcggcctctg ctcccgggtc tgacactgtc     1020
agcgacgtgg aacaagaact gaagaagggt gcggtcgttg tcgaagaagc tccaaagcca     1080
aaggctcttt cgccgcctgc agcccccgct gtacaagaag acctttggga tttcaagaaa     1140
tacattggtt tcgaggagcc cgtggaggcc aaggatgatg gccgggctgt cgcagatgat     1200
gcgggctcct ttgaacacca ccagaatcac gactccggac cttttggcagg ggagaatgtc     1260 atgaacgtgg tcgtcgtggc tgctgagtgt tctccctggt gcaaaacagg catggacatt     1320
acctcttcag tctctcttcc tgttgttcat aaaactttgc tcgaattact cataagaaca     1380
aacattgtgt tgcataggtg gtctgggaga tgttgcgggt gctctgccca aggctttggc     1440
aaagagagga catcgtgtta tggtactaca agctttcatt taactctgtt gggtccatat     1500
gttcgaataa tatcagtgag tagtataatg ttattaagtg caagacatga aagtgttctt     1560
ttgtcatact ccctccgtaa attaatataa gagcgtttag attactactt tagtgatcta     1620
aacgctctta tagtagttta cagacggagt agagtatttc atagccaacc ctggaggtta     1680
ggttgctgag gcctactggg tggggaggg ggtttgaaac aagtggtggt tagcagccag      1740
atttcacaaa gaaggaggct gataaccaca ccatcagtga aggaatgaat gtcgggtacc     1800
cgatcgaccg ttttgcccaa cgtcgggttt acccgcccta tagatccgaa taagtagttc     1860
ctatcttcaa ttaggtacca aatatcgcca gcgcccgtgt gtgtatttat actactggat     1920
gatcaattta tcaacatttc cggttaatgg tttctatcat attcactgta attgttagta     1980
aacagtagat gtttgtaatg tagatgatgg ataaatgtat gttgtcgagc tttcatttca     2040
atgcaatttt gattgggagc tagtttcgcg gttcggttag agccatcaaa accccagaat     2100 tttgggagt tggcttgtga gagagggttt tggggagtta actttcggga ttcagttaga     2160
gacgctctta ctagttccag taaagagtaa actatttcct gcaggcatcc caattattct     2220
gtagaaatta gaagtggaaa atagttatgg tatcatataa accatatatt attcaaaatc     2280
tagaatcatg gacttggcta gactttgata atctgaaatt ttaaatttga tgataattga     2340
gaaatgatcc tttctatctt aggttgtggt accaaggtat ggggactatg aagaagccta     2400
cgatgtcgga gtccgaaaat actacaaggc tgctggacag gtaagcaaaa atgcaatcga     2460 agggagctg aaattttatt gcttattgtc ataataaatc aatttttaag tgtttttttt     2520
gtcctgcagg atatggaagt gaattatttc catgcttata tcgatggagt tgattttgtg     2580
ttcattgacg ctcctctctt ccgacaccgt caggaagaca tttatggggg cagcagacag     2640
gttaatcttc tatatgttgg tgtttgattg cactgataaa ctgagaacaa gccaaggcct     2700
actgactggc atatgattac acattttatt ttttcaggaa attatgaagc gcatgatttt     2760
gttctgcaag gccgctgttg aggtatctct ccaactcaat tgacaaccta ttaccactat     2820
acaattatgt gtatgcatgt atttcaacag atacataatc tcttgtgaag tgcatatata     2880
ctaataacat ttcaataacct tacatgcaca tttggtcaag cgttatgatt taacttctga     2940
```

```
taatctattg cactgatgaa caattatctt gatgatcctt gttacttcat cgttatgttt    3000
ccatgttctc ttcaccgcga attgatttgg aaatagcatt tccacctgcc acaaacaata    3060
atatacactc ctactttcat ccaatttaga tattttcgta cttggcatat catcccatta    3120
aatattattg gtccatcatt tttattcctc tataatttgc aggttccatg gcacgttcca    3180
tgcggcggtg tcccttatgg ggatggaaat ctggtgttta ttgcaaatga ttggcacacg    3240
gcactcctgc ctgtctatct gaaagcatat tacagggacc atggtttgat gcagtacact    3300
cggtccatta tggtgataca taacatcgct caccaggttc ctttttctcct aatcttgatt    3360
tttctctagt ctctactatt tactccacat tgtttgagga aactaaacgg gttgcaaaat    3420
tatgatggct tatgaaagtt atagtcttat agaggtaaat gcaccagtgg tgcttgaact    3480
tgtcacgcgt gttcactttg gtgcttacag ttgtagacta tgaaaaacgg gtgcaaaaac    3540
ttgctgttgt gtgccatacg gtgcatttttc cgtatgtagg agtcaaacgt tgcctatgtg    3600
ggcattgtat tcccgtctat agctgttaga ccgtgcctac gtcgccattg gcccacaca    3660
ctctctattt acatgtgggc cccacttgtc aacctatgac ataaataaat ggaaatttat    3720
aataaaaatg atggcctggg gtcttgaaaa tgggacctcg caggtatgct ggtagccagc    3780
acgccctaaa cattaatccc ctatgcactt catgtcttgt gtatgtgtgt gtctgtgtgg    3840
ggagggggg ggtatgtatg cttatatcct ttgctccaag gctaccatcc tcaacaagcc    3900
cacctccgct tcaacacggc cagcgccttc atgatggccc aggtgctccg caccatcgct    3960
caaagcggca acgtcgttgt catgaccatc caccaaccca acacacaaaa tcctcaacat    4020
ccgcaaatag tgagcatgcc cctcttgtcc tttcccctcg tacccaaaca tgtcttgata    4080
acccttggag ctgcacaagt tgtgaccatc gcctgcgtcg cctcatagag cccgacctag    4140
ccggaccgtt atagaagcct acttgggagc ccatacctcc ctgcacatcc tcctcttttcc    4200
ccatagatcg tgccgccatc gcaaaccaac ttctcctctc cttctcccac tctggccgtt    4260
tccccgccg cgaagctgca atacatgccg agttggccat ggccctattc cccaattgct    4320
cgcactagga ggtcctcctc taagcctagc accttttccc ctcaccaatt gcaagttggg    4380
gagcccctcg cgagctccct acgtcggctg cagttgcctg ccgcctcaac tctgatccag    4440
acctcgttcc cgtggcctcg gcgacatctc ctcgacctcc cattccacac gtggcctggc    4500
gaggatcacc gcatgttcat ccatgtgaac cgaatcatca tagaactaac accggagagg    4560
tcatcccgac ggcgtcgcac tgttcctcta ttccccccaa gccgtgtcgc gtcataatat    4620
aagacggact tatttgtatc ccttgggtca tcggttcaat ggctatttct ttctcctgtc    4680
tactgataag tgggacccac acgccacact aagcccttttc tttctcctac ccgttgataa    4740
gtgggacccca cacacagtac ttagccagag agagaacatg agcttgttgg tgccacgtcg    4800
gcaagccatg tcagcagtct taacggctac aaacaacgga tatggtgtca cgtgagcgtt    4860
tacgaatgga aagtgcatca tactgcatgc gagagccaga gccaggtttt tgcaccagtt    4920
ttctgtatttt tacaactgcg agcatcaaag tgtacatatg ccgaaccaaa gtgaacatgg    4980
tgagtccatt ctttttctggt gcggtgggtg gctcaaagac accccaatag aagctattgc    5040
ctccgacatt gccaattcgg tgccgaacca tattgaagtg gtgaggtcag ttgcttgtgc    5100
tatgactact aggtattgga tgagggacat aaaggatctc ataaatattg caatgttcat    5160
tcaaattctt aacatttgcg aagcgcttca tgatttccat ctcccctaga tcagagacac    5220
ttggtcgtgt acactgaatt tctcaggtcg cttctcgtct aaatccgcat atgtagctca    5280
cttcaatgac ttgcctttgg tccagctaac gccatttgcg tagcaaattt ttcatatggc    5340
```

```
tcgctctgcg caagaggatt tggatcacgg gcagacgcgc tagacaaggt cttccgcaca    5400
atgaacattg agttttttga tccgctcttc ccgaagacac ttgtgatctt attacgagtt    5460
gtgccatttc aaacatctgt ctctccatgg tcgccccagc catagatgcc ttgttctctg    5520
aatggtgggt ttcagctagg aacagggtgc caccttcgga caagaagttg cgtagtttgg    5580
tcgtcttaac tgcttggttg atttggaagg aacacaacaa cagtctttga aggcaaagct    5640
aattccttcg atcaagttat tagacggatc aagtgtgatg aatcctactg gtacaatgcc    5700
gttgctagtt gcttggagtc actatttggc taggtcgctt gccatcccgc tctgtgctaa    5760
gcgcttgggg tcgcttttgc tcaatttgta ttttgttgtt atgtgttttt agtaatgtaa    5820
cctgaacttt ctggactaag tagaaaaaaa ttctcctcca taatgatcac atacagttct    5880
cctgcatggt tcgaaaaaaa aatgagaaca tccgtgcaa gtttaagcac caccggtgca    5940
tttttacctc aaagttatat acaacactga catgccgaat tacatgcttt ggtcagttat    6000
tccattcttc ggtactccgt tgggctaatt cttttctcttc atgttgcatg cagggccgtg    6060
gccctgtaga tgaattcccg ttcaccgagt tgcctgagca ctacctggaa cacttcagac    6120
tgtacgaccc cgtgggtggt gaacacgcca actacttcgc cgccggcctg aagatggcgg    6180
accaggttgt cgtggtgagc cccgggtacc tgtgggagct gaagacggtg gagggcggct    6240
gggggcttca cgacatcata cggcagaacg actggaagac ccgcggcatc gtcaacggca    6300
tcgacaacat ggagtggaac cccgaggtgg acgcccacct caagtcggac ggctacacca    6360
acttctcct gaggacgctg gactccggca agcggcagtg caaggaggcc ctgcagcgcg    6420
agctgggcct gcaggtccgc gccgacgtgc cgctgctcgg cttcatcggc cgcctggacg    6480
ggcagaaggg cgtggagatc atcgcggacg ccatgcccctg gatcgtgagc caggacgtgc    6540
agctggtgat gctgggcacc gggcgccacg acctggagag catgctgcag cacttcgagc    6600
gggagcacca cgacaaggtg cgcggggtggg tggggttctc cgtgcgcctg gcgcaccgga    6660
tcacggcggg ggcggacgcg ctcctcatgc cctcccggtt cgagccgtgc gggctgaacc    6720
agctctacgc catggcctac ggcaccgtcc ccgtcgtgca cgccgtcggc ggcctcaggg    6780
acaccgtgcc gccgttcgac cccttcaacc actccgggct cgggtggacg ttcgaccgcg    6840
ccgaggcgca caagctgatc gaggcgctcg ggcactgcct ccgcacctac cgagacttca    6900
aggagagctg gagggccctc caggagcgcg gcatgtcgca ggacttcagc tgggagcacg    6960
ccgccaagct ctacgaggac gtcctcgtca aggccaagta ccagtggtga              7010
```

<210> SEQ ID NO 13
<211> LENGTH: 25
<212> TYPE: DNA
<213> ORGANISM: Artificial Sequence
<220> FEATURE:
<221> NAME/KEY: modified_base
<222> LOCATION: 1..1
<223> OTHER INFORMATION: coupled to FAM-a
<220> FEATURE:
<221> NAME/KEY: modified_base
<222> LOCATION: 25..25
<223> OTHER INFORMATION: coupled to a-TAMRA
<220> FEATURE:
<223> OTHER INFORMATION: PCR probe

<400> SEQUENCE: 13
ctcctgcctg tctatctgaa agcat                                          25

```
<210> SEQ ID NO 14
<211> LENGTH: 6898
<212> TYPE: DNA
<213> ORGANISM: Triticum aestivum
<220> FEATURE:
<221> NAME/KEY: CDS
<222> LOCATION: join(247..510, 602..1307, 1396..1460, 2277..2354,
      2444..2554, 2652..2696, 3080..3253, 5942..6898)
<223> OTHER INFORMATION: Triticum aestivum wSSII-A gene for starch
      synthase II-A, complete cds.

<400> SEQUENCE: 14
```

| | | | | | |
|---|---|---|---|---|---|
| gggggccgtt | cgtacgtacc | cgcccctcgt | gtaaagccgc | cgccgtcgtc | gccgtccccc | 60 |
| gctcgcggcc | atttccccgg | cctgaccccg | tgcgtttacc | ccacagagca | cactccagtc | 120 |
| cagtccagcc | cactgccgcc | gcgctactcc | ccactcccgc | tgccaccacc | tccgcctgcg | 180 |
| ccgcgctctg | ggcggaggac | caacccgcgc | atcgtaccat | cgcccgcccc | gatcccggcc | 240 |
| gccgccatgt | cgtcggcggt | cgcgtccgcc | gcgtccttcc | tcgcgctcgc | ctccgcctcc | 300 |
| cccgggagat | cacgcaggcg | ggcgagggtg | agcgcgccgc | caccccacgc | cggggccggc | 360 |
| aggctgcact | ggccgccgtg | gccgccgcag | cgcacggctc | gcgacggagg | tgtggccgcg | 420 |
| cgcgccgccg | ggaagaagga | cgcgagggtc | gacgacgacg | ccgcgtccgc | gaggcagccc | 480 |
| cgcgcacgcc | gcggtggcgc | cgccaccaag | gtagttggtt | cgttatgact | tgctgtatgg | 540 |
| cgcgtgcgcc | tcgagatcag | ctcacgaatt | gtttctacaa | aacgcacgcg | ctcgtgtgca | 600 |
| ggtcgcggag | cggagggatc | ccgtcaagac | gctcgatcgc | gacgccgcgg | aaggtggcgc | 660 |
| gccggcaccg | ccggcaccga | ggcaggacgc | gcccgtccca | ccgagtatga | acggcacgcc | 720 |
| ggtgaacggt | gagaacaaat | ctaccggcgg | cggcggcgcg | accaaagaca | gcgggctgcc | 780 |
| cgcacccgca | cgcgcgcccc | atccgtcgac | ccagaacaga | gtaccagtga | acggtgaaaa | 840 |
| caaagctaac | gtcgcctcgc | cgccgacgag | catagccgag | gtcgtggctc | cggattccgc | 900 |
| agctaccatt | tccatcagtg | acaaggcgcg | ggagtccgtt | gtcccagccg | agaagccgcc | 960 |
| gccgtcgtcc | ggctcaaatt | tcgtggtctc | ggcttctgct | cccaggctgg | acattgacag | 1020 |
| cgatgttgaa | cctgaactga | gaagggtgc | ggtcatcgtc | gaagaagctc | caaacccaaa | 1080 |
| ggctcttttcg | ccgcctgcag | cccccgctgt | acaagaagac | ctttgggact | tcaagaaata | 1140 |
| cattggcttc | gaggagcccg | tggaggccaa | ggatgatggc | tgggctgttg | cagatgatgc | 1200 |
| gggctccttt | gaacatcacc | agaaccatga | ttccggacct | ttggcagggg | agaacgtcat | 1260 |
| gaacgtggtc | gtcgtggctg | ctgaatgttc | tccctggtgc | aaaacaggca | tggacattac | 1320 |
| ctcttcagtc | tctcttcccg | ttgttcataa | aactttgctc | gaatcactca | taagaacaaa | 1380 |
| cattgtgttg | cataggtggt | cttggagatg | ttgcgggtgc | tctgcccaag | gctttggcaa | 1440 |
| agagaggaca | tcgtgttatg | gtactgcagg | cttttcactta | actctgttga | gtccatatgt | 1500 |
| tcgaataata | tcagtgattg | gcataatgtt | attaagtgca | agacatgaaa | gtgttcttct | 1560 |
| gttagagtat | ttcatagcca | accctggagg | ttaggttgtt | ggggcctact | gggtgcggga | 1620 |
| gggggtttgc | aaaaagtggt | ggttagcagt | cggatttcac | aaataaggag | gctgataacc | 1680 |
| acgccatcag | tgaagggaat | gagtgtcggg | tacccgatcg | accgttttgc | ccgacgtcag | 1740 |
| gtttacctgc | cctgtagatc | cgaataagta | gttcctatcc | tcagttaagt | accaaatatc | 1800 |
| gccagcaccc | gtgtgtgtat | ttatagtact | ggatgatcaa | tttatcaaca | tttccggtta | 1860 |
| atggttgcta | tcatattcac | tgtaattgtt | agtaaacagt | ggatgtttgt | aatgtagatg | 1920 |
| atggctaaat | gtatgttgtc | aagctttcat | tttaaagaaa | attttattgg | gagctagttt | 1980 |

-continued

```
tcgggtttgg ttagagccac caaaacccca gaattttttgg gagttggctt gtgacagagg    2040
gttttgggga gttaactttc gggattcagt tagagacgct cttactagtt ccagtaaaga    2100
gtaaactatt ttctgcagtc atcccaattg ttctgtagaa attaaaagta gaaaatagtt    2160
gtggtatcat ataaaccata tattattcaa aatctagaat catggacttg gctagctttt    2220
gatgatctga aatttttaaat ttgatgataa ttgagaaatg atcctttcta tcttaggttg    2280
tggtaccaag gtatggggac tatgaggaag cctacgatgt cggagtccga aaatactaca    2340
aggctgctgg acaggtaagc gaaaatgcaa tcaaagggga gctgaaattt caatgcttac    2400
tatcataata aatcaatttt aagtaaaaaa atttgtcctg caggatatgg aagtgaatta    2460
tttccatgct tatatcgatg gagttgattt tgtgttcatt gacgctccta tcttccgaca    2520
ccgtcaggaa gacatttatg ggggcagcag acaggttaat tttctatatg ttggtgtttg    2580
attgcactga taaactgaga ataagccaag gcctactgac tggcatatga ttacacattt    2640
tattttttca ggaaattatg aagcgcatga ttttgttctg caaggccgct gtcgaggtat    2700
cctctccaac tcaattgaca acctattacc actatacaat tatgtgtatg catgtatttc    2760
aacagatacg taatctccct tgtgaagtgt atatatacta ataacatttc aatacctcac    2820
atgcacattt ggtcaagcgt tatgatttaa cttctgataa tctattgcac tgatgaacaa    2880
taatattgat gatccttgtt acttcatcgt tatgtttatg ttctcttcac cggcgcattg    2940
attttggaaa tagcatttcc acctgccaca aacaataata tatactccta ctttcatcca    3000
atgtagatat tttcgcactt ggcatatcat cccattaaat attattggtc catcattttt    3060
attcctctat aatttgcagg ttccttggca cgttccatgc ggcggtgtcc cttatgggga    3120
tggaaatctg gtgtttattg caaatgattg gcacacggca ctcctgcctg tctatctgaa    3180
agcatattac agggaccatg gtttgatgca gtacactcgg tccattatgg tgatacataa    3240
catcgcgcac caggttcctt ttctcctaat cttgttttttt ctctagtctc tactattcac    3300
tccacattgt ttgaggaaac taaaggggtt gcaaaattat gatggcttat gaaagttatg    3360
gaggtaaatg catcagtggt gcttgaactt gtcacgcatg ttcactttgg tgcttacagt    3420
tgtagactac ggaaaactgg tgcaaaaact tggctattgt gtgcaatacg gtgtattttc    3480
cgtatgtagg gtcaaatgtt gcctatgtgg cattgtattc ccgtctatag atgttagacc    3540
gtgcctacat cgccattggg cccacacact ccctattaca tgtgggaccc acttgtcagc    3600
ctatgacata aataaaatgg aaatttataa taaaaatgat ggcctggggt cttgaaaatg    3660
ggacctcgca ggtatgccgc tagccagcac gccctaatca ttaatcccct atgcacttca    3720
gtatgtgtgt gtctgtgtgt ggagtcgggg ggggggggg tatgtattct tatatccttt    3780
gctctaaggc tatcattggc gtgctagcac cgccgggtct ccatcaacac cgacatcatc    3840
cacgacccca tccagctctt cctcaacaag cccacctcca gcctcaactc gggcagcacc    3900
ttcatggtgg cctaggtgct ctgcaccatc gctcgaagtg gcaacgtcgt tgtcatgacc    3960
atccaccaac ccaacacgca aaatcctcaa catcatttga cagtgagcat gcccctcttg    4020
tcatttcccc ctcatacccca aacctgtctc gataacccttt ggagctgcac aagttgtgac    4080
catcgcctgc gtcgctgcac aacgcctgac ctagccggac cattatagaa gcctgccttg    4140
ggagcccata cctccctgca catcctcctc tttccccata gaccgtgccg ccatcgcaaa    4200
tcgacttctc ctctcctcct tctcctgctc tggccgtttt cccgccgcg aagctgcaat    4260 ccatggcgag ttggccatgg ccctattccc caattgctcg cactaggagg tcctccttga    4320
agcctagcac cttttccccct cactaattgc aagttgggga gccccctcacg agctccctac    4380
```

```
attggccgta gtcgcctgcc gcctcaactc tggtccagac ctcgttcccg tggcctcgac      4440
gacatctcct cgacctccca ttccacacgc ggcctggaga ggatcaccgc atgttcatcc      4500
atccgacccg aatcatcata gaaccaacgc cagagaggtc atcccgacga cgtcgcactg      4560
ttcctctatt tcccccaagc tgtgtcgcgt cataatataa gacgggcttg tttgtatctc      4620
taggggtcat cgggttcaat ggctagctca tgcatggacc tgactttagg tcccaggttc      4680 gaaccccgc gtgcacataa tttatttgct atttatttct cctatctact aataagtggg      4740
acccacacat catactaagc ccttttttgtc tcttgcctgc tgataagtgg gacccacacg      4800
caatacttag ccagagagag aacatgagct tgttggtgcc gcgttggcaa gccacgccag      4860
cagtcttaac ggctacaaac agaggatatg gtgtcacatc aacgtgcaga gcgtttacga      4920
atggaaagtg tactatatgc acacaagagc cagagccagg tttttgcacc agttttttgt      4980
attctacaac tgcgagcacc aaagtgtaca tgccgaacca aagtgaacac ggcgagtcca      5040
ttcttttctg gtacgatggg tggctcaaag acaccccaat agaagctatc acctcggaca      5100
ttgccaattg ggtgccgaac tacattaaag tggcaaggtc agttgattgc gctatgtgtt      5160
ggatcaggga cataaacgat tccataaata ttgcaatgtt cattcaaatt cttaacattt      5220
gcgaggcgct tcatgatttc catctccctc atatcagaga catttggtcg tgtacactaa      5280
atttctcagg tcacttctcg tctaaatccg catatgtagc tcacttcaat gacttgactt      5340
tggtccagct aacgccattt ggcgctcttg ggccccttttg cgtagcaatt ttttcatatg      5400
gctcgctccg cgcaataagga tttggatcac gggcagacgc gctagatgag gtcttccaca      5460
caatgaacat tgcgttcttt gctctgctct tccagaagac acttgtgatt ttattacgag      5520
ttgtgccata gatgccggtg ggtttcagct aggaacaggg tgtcaccttc ggacaagaag      5580
aagttgcata gtttggtcgt cttaactgct tggtcgattt ggaaggagca caacaacagt      5640
ctttgaaggc aaagctaatt ccctcgatca agttattaga cggatcaaat gtggtacagt      5700
gccatggcta gttgcttgga gtcacttttta agctaggtcg cttgccatca cgctttgtgt      5760
taagcgcttg gggtcgcttt tgctcaattt gtattttgtt gttatgtgtt tttagttatg      5820
tagcctgaac tttctggact tagttttttc ctctataatg atcacatgct ttggtcagtt      5880
attcctttct tgggtactcc gttgggctaa ttctttctct tgattgatgt tgtatatgca      5940
gggccgtggc ccagtagatg aattcccgtt caccgagttg cctgagcact acctggaaca      6000
cttcagactg tacgaccccg tgggtggtga gcacgccaac tacttcgccg ccggcctgaa      6060
gatggcggac caggttgtcg tggtgagccc cgggtacctg tgggagctca agacggtgga      6120
gggcggctgg gggcttcacg acatcatacg gcagaacgac tggaagaccc gcggcatcgt      6180
caacggcatc gacaacatgg agtggaaccc cgaggtggac gtccacctcc agtcggacgg      6240
ctacaccaac ttctcccctga gcacgctgga ctccggcaag cggcagtgca aggaggccct      6300
gcagcgcgag ctgggcctgc aggtccgcgc cgacgtgccg ctgctcggct tcatcggccg      6360
cctggacggg cagaagggcg tggagatcat cgcggacgcc atgccctgga tcgtgagcca      6420
ggacgtgcag ctggtcatgc tgggcaccgg ccgccacgac ctggagagca tgctgcggca      6480
cttcgagcgg gagcaccacg acaaggtgcg cgggtgggtg gggttctccg tgcgcctggc      6540
gcaccggatc acgcgggcg ccgacgcgct cctcatgccc tccggttcg agccgtgcgg      6600 gctgaaccag ctctacgcca tggcctacgg caccgtcccc gtcgtgcacg ccgtcggcgg      6660
gctgagggac accgtgccgc cgttcgaccc cttcaaccac tccggcctcg ggtggacgtt      6720
cgaccgcgcc gaggcgcaca agctgatcga ggcgctcggg cactgcctcc gcacctaccg      6780
```

```
ggactacaag gagagctgga ggggcctcca ggagcgcggc atgtcgcagg acttcagctg    6840
ggagcatgcc gccaagctct acgaggacgt cctcctcaag gccaagtacc agtggtga     6898
```

METHOD FOR QUALITATIVE AND QUANTITATIVE DETECTION OF COMMON WHEAT

CROSS REFERENCE TO RELATED APPLICATIONS

This application is a National Stage of International Application No. PCT/JP2010/072806 filed Dec. 17, 2010, claiming priority based on Japanese Patent Application No. 2009-289340, filed Dec. 21, 2009, the contents of all of which are incorporated herein by reference in their entirety.

TECHNICAL FIELD

The present invention relates to a method that specifically detects common wheat using a PCR procedure. The present invention specifically relates to a method for the specific qualitative and/or quantitative detection of common wheat in a sample of interest, e.g., a food raw material or processed food. The present invention further relates to a method that can determine whether the wheat in a sample of interest is common wheat or a wheat other than common wheat, for example, durum wheat, and that can detect the presence of both wheat and a non-common wheat. The present invention further relates to a primer set, a nucleic acid probe, and a detection kit for use in the aforementioned detection methods.

BACKGROUND ART

Consumers are taking a strong interest in food labeling regulations and systems against a backdrop of concerns about safety and security of food. The labeling of food has become essential in terms of allowing consumers to evaluate and select food quality themselves. Wheat is converted into a variety of products through various processes and is also distributed in the marketplace. The labeling for macaroni, which is a typical product, is established by the Labeling Standards for Processed Food Quality and the Labeling Standards for Macaroni Quality, and "durum wheat semolina", "durum wheat flour", "strong wheat farina", and "strong wheat flour" are displayed in descending order of content for the raw wheat flours used. Excluding tracking surveys for production processes, no technology exist that is capable of qualitatively and/or quantitatively discriminating common wheat from durum wheat in such processed wheat foods, and there is demand for the development of such technology.

To date, methods have been formulated for the specific and highly sensitive detection of wheat using various technologies. These methods can basically be classified into methods that use wheat-derived protein or DNA in the sample of interest as the detection target.

The methods for the detection of protein can be exemplified by electrophoretic methods, western blotting methods, and immunochemical methods, and by methods that are combinations of the preceding. In particular, ELISA methods have enjoyed broad commercial acceptance due to the availability of the peripheral equipment and reagents.

However, the ancestries of common wheat and durum wheat share a very strong commonality and their respective constituent components are thus also quite similar. The protein is no exception here, and while there are differences in the protein component ratios, there are almost no differences in the types of proteins present in these wheats. It is thus quite difficult to discriminate between common wheat and durum wheat using protein levels.

On the other hand, several technologies have also been devised for the specific detection of wheat using PCR, which is a gene amplification technology. However, the analysis of wheat DNA or genes is not always entirely adequate and this has made the development of an optimal testing method quite problematic.

Non-Patent Document 1 reports a wheat detection method that employs PCR and that targets the Wx-D1 gene encoded in the wheat D genome. This test method is capable of the very high-specificity detection of common wheat and is optimal for testing processed wheat products such as plant, grain, and wheat flours. Durum wheat, which lacks the D genome, is not detected by this test method.

Patent Document 1, on the other hand, discloses a PCR-based method that qualitatively and/or quantitatively detects wheat and that targets the starch synthase II (SSII) gene encoded in the wheat A, B, and D genomes. This detection method targets a common region of SSII A, B, and D and is capable of the specific and highly sensitive detection of wheat. A primer set that specifically discriminates SSII-D is disclosed in Patent Document 1, but the specificity is not necessarily assured and it is also unsuitable for quantitative measurements.

Non-Patent Document 2 reports that the starting genome undergoes physical cleavage in food processing steps at medium or high intensity, such as heating. When the PCR amplification target region in the wheat genome is long, the occurrence of cleavage therewithin brought about by the processing step may prevent the value measured by quantitative PCR from expressing the actual wheat content. As a result, a strategy must be devised for reducing the likelihood that the PCR target region will undergo fragmentation even when the wheat genome has been subject to fragmentation due to the application thereto of medium- or high-intensity processing.

Accordingly, there is desire for a method capable of the highly specific and highly sensitive detection of common wheat in a food raw material or a processed food product. In addition, since a suitable method does not yet exist for qualitatively and/or quantitatively discriminating between and detecting common wheat and a non-common wheat, for example, durum wheat, in a food raw material or a processed food, there is demand for the development of such a detection method.

Patent Document 1: Japanese Patent Application Laid-open No. 2009-5588

Non-Patent Document 1: Iida, M. et al., Development of taxon-specific sequences of common wheat for the detection of genetically modified wheat. *J. Agric. Food Chem.*, 2005 Aug. 10; 53(16):6294-300.

Non-Patent Document 2: Yoshimura, T. et al., Comparative studies of the quantification of genetically modified organisms in foods processed from maize and soy using trial producing. *J. Agric. Food Chem.*, 2005 Mar. 23; 53(6): 2060-9.

DISCLOSURE OF THE INVENTION

An object of the present invention is to provide a specific and highly sensitive method for qualitatively and/or quantitatively detecting common wheat in the wheat present in a sample of interest, e.g., a food raw material or a processed food. A further object of the present invention is to provide a method that can qualitatively and/or quantitatively discriminate and detect between common wheat and non-common wheat, e.g., durum wheat, in a food raw material or a processed food.

A further object of the present invention is to provide a primer set, a nucleic acid probe, and a detection kit that can be used in the aforementioned detection methods that use a PCR procedure.

As a result of intensive and extensive investigations in order to achieve these objects, the present inventors discovered a specific nucleic acid sequence in the starch synthase II-D located on the wheat D genome (abbreviation: SSII-D) and also discovered that the specific and high-sensitivity detection of common wheat in the wheat in a sample of interest could be achieved by designing a primer set based on this nucleic acid sequence and carrying out a PCR procedure using this primer set. Furthermore, in order to discover an effective nucleic acid probe for implementing a quantitative PCR procedure, the present inventors designed a special nucleic acid probe from within the nucleic acid sequence of the region bracketed by this probe set on the SSII-D gene.

The present inventors also discovered that it was possible to discriminate between common wheat and non-common wheat, e.g., durum wheat, in a sample of interest by combining the aforementioned common wheat detection method with a method for detecting a broad range of wheats through the specific and highly sensitive detection of a common region of the SSII located on the wheat A, B, and D genomes and by carrying out a relative comparison and/or an absolute comparison of the results obtained by these methods.

The wheat genome is composed of three genomes designated A, B, and D, and each of these has seven chromosomes. Common wheat is an AABBDD hexaploid and durum wheat is an AABB tetraploid. To date, a large number of wheat genes are identical and information has also been accumulated on the conformation of these genes, but this information is not always entirely adequate.

Among the preceding, the present invention has focused in particular on starch synthase II (abbreviated as SSII-A, SSII-B, and SSII-D), whose conformation has been determined in each of the genomes A, B, and D. It has been reported that these SSII's are encoded on the short arm of chromosome 7 in each of the wheat genomes A, B, and D (Shimbata, T. et al., Mutations in wheat starch synthase II genes and PCR-based selection of a SGP-1 null line. *Theor. Appl. Genet.*, 2005 October; 111(6): 1072-9).

Subtle differences exist among the SSII base sequences encoded in the individual A, B, and D genomes, and it is also possible to specifically discriminate each of SSII-A, B, and D through the primer set design process. Synthesizing this information, the conclusion was drawn that it would be possible to specifically detect the common wheat group, which has the D genome, by discovering a characteristic base sequence that exhibits subtle differences among SSII-A, SSII-B, and SSII-D.

Thus, the detection of common wheat in a sample of interest was achieved by selecting a base sequence that is characteristic of the SSII-D located on the D genome present in common wheat but that does not crossreact to other plants or durum wheat, which lacks the D-genome; designing a nucleic acid probe and a primer set that complementarily hybridize to this nucleic acide sequence; and implementing a PCR procedure using the preceding. In addition, the ability to qualitatively and/or quantitatively discriminate between common wheat and non-common wheat, e.g., durum wheat, in the wheat in a sample of interest was achieved by implementing the PCR procedure indicated above; implementing a previously developed method, i.e., a PCR procedure targeted to SSII-A, B, and D common region, on the same sample; and carrying out a relative comparison and/or an absolute comparison of PCR amplification product expression by these two PCR procedures.

Accordingly, the present invention is a method for detecting the presence of common wheat in a sample of interest, wherein the method includes: implementing a PCR procedure using a primer having the base sequence shown by SEQ ID NO:5 and a primer having the base sequence shown by SEQ ID NO:6, with a nucleic acid extracted from the sample of interest being used as a template; and detecting the presence of a PCR amplification product. Here, the presence of a PCR amplification product can be confirmed by known methods, for example, by an electrophoresis technique, and the presence of common wheat is then confirmed when the PCR amplification product is observed.

The present invention is also directed to a method for qualitatively and/or quantitatively detecting the presence of common wheat by carrying out a quantitative PCR procedure using the primer set described above and a specific nucleic acid probe. The present invention therefore is a method for qualitatively and/or quantitatively detecting the presence of common wheat in a sample of interest by implementing a quantitative PCR procedure using a primer having the base sequence shown in SEQ ID NO:5, a primer having the base sequence shown in SEQ ID NO:6, and a nucleic acid probe having the base sequence shown in SEQ ID NO:11, with a nucleic acid extracted from the sample of interest being used as a template.

In an embodiment of this method according to the present invention, the nucleic acid probe having the base sequence shown in SEQ ID NO:11 is specifically a labeled nucleic acid probe and the presence of common wheat can be qualitatively and/or quantitatively detected by obtaining an amplification curve during the PCR by monitoring a signal corresponding to the amount of amplification product and generated by the labeled nucleic acid probe.

In an embodiment of the above-described method, a quantitative PCR procedure is preliminarily carried out on serially diluted standard samples to obtain amplification curves; a threshold cycle (Ct value) is determined by establishing a suitable threshold; a calibration curve is then constructed in advance as a function of the initial amount of template; and the initial amount of template in a sample of interest is determined using this calibration curve. Accordingly, a further embodiment is the quantitative detection, when the aforementioned quantitative PCR procedure is run, of the presence of common wheat using a preliminarily constructed calibration curve.

The present invention is also directed to a primer set comprising a primer having the base sequence shown by SEQ ID NO:5 and a primer having the base sequence shown by SEQ ID NO:6, to a nucleic acid probe having the base sequence shown by SEQ ID NO:11, and to a nucleic acid probe having the base sequence shown in SEQ ID NO:11, has a 5' terminal modified by a fluorophore, and has a 3' terminal modified by a quencher.

The present invention is also a method of detecting the presence of common wheat and/or a wheat other than common wheat in a sample of interest, comprising:

(1) preparing a nucleic acid sample by extracting a nucleic acid from the sample of interest,
  (a) detecting the presence of common wheat by implementing a quantitative PCR procedure using this nucleic acid sample, a primer having the base sequence shown in SEQ ID NO:5, a primer having the base sequence shown in SEQ ID NO:6, and a nucleic acid probe having the base sequence shown in SEQ ID NO:11 and obtaining an amplification curve by monitoring a signal that corresponds to the amount of amplification product which is generated by the nucleic acid probe, and (b) detecting the presence of wheat by implementing a quantitative PCR procedure using the aforementioned nucleic acid sample, a primer having the base sequence shown in SEQ ID NO:9, a primer having the base sequence shown in SEQ ID NO:10, and a nucleic acid probe having the base sequence shown in SEQ ID NO:13 and obtaining an amplification curve by monitoring a signal that corresponds to the amount of amplification product which is generated by the nucleic acid probe; and (2) comparing the results of (a) with the results of (b).

In an embodiment of the aforementioned method, quantitative PCR is preliminarily carried out on serially diluted standard samples to obtain amplification curves; a Ct value is determined by establishing a suitable threshold; a calibration curve is then constructed in advance as a function of the initial amount of template; and the initial amount of template in a sample of interest is determined using this calibration curve.

Accordingly, in an embodiment of the aforementioned method, (1) in (a), an amplification curve is obtained by monitoring a signal that corresponds to the amount of amplification product which is generated by the nucleic acid probe and the presence of common wheat is quantitatively detected using a calibration curve that has been constructed in advance, and in (b), an amplification curve is obtained by monitoring a signal that corresponds to the amount of amplification product which is generated by the nucleic acid probe and the presence of wheat is quantitatively detected using a calibration curve that has been constructed in advance; and (2) comparing the quantitative value of (a) with the quantitative value of (b).

In this method, for example, when the presence of common wheat is detected in (a) and this quantitative value is compared with the quantitative value for wheat from (b) and the quantitative value from (a)<the quantitative value from (b), this difference can then be inferred to be due to non-common wheat in the sample of interest. In addition, when a PCR amplification product is not detected in (a) while a PCR amplification product is detected in (b), this confirms that common wheat is not present in the sample of interest while a non-common wheat, e.g., durum wheat, is present.

With regard to the specific execution of the aforementioned method for detecting the presence of common wheat and/or non-common wheat, both the nucleic acid probe having the base sequence shown in SEQ ID NO:11 and the nucleic acid probe having the base sequence shown in SEQ ID NO:13 can be labeled nucleic acid probes. More specifically, the nucleic acid probe having the base sequence shown in SEQ ID NO:11 can be a nucleic acid probe modified at its 5' terminal by a fluorophore and modified at its 3' terminal by a quencher and the nucleic acid probe having the base sequence shown by SEQ ID NO:13 can be a nucleic acid probe modified at its 5' terminal by a fluorophore and modified at its 3' terminal by a quencher.

The present invention is also directed to the following kits for executing the aforementioned detection methods: (i) a common wheat detection kit comprising a primer set of a primer having the base sequence shown in SEQ ID NO:5 and a primer having the base sequence shown in SEQ ID NO:6; (ii) a common wheat detection kit comprising a primer set of a primer having the base sequence shown in SEQ ID NO:5 and a primer having the base sequence shown in SEQ ID NO:6, and a nucleic acid probe having the base sequence shown in SEQ ID NO:11, that is modified at its 5' terminal by a fluorophore, and that is modified at its 3' terminal by a quencher; and (iii) a common wheat detection kit comprising a primer set of a primer having the base sequence shown in SEQ ID NO:5 and a primer having the base sequence shown in SEQ ID NO:6, a nucleic acid probe having the base sequence shown in SEQ ID NO:11, that is modified at its 5' terminal by a fluorophore, and that is modified at its 3' terminal by a quencher, a primer set of a primer having the base sequence shown in SEQ ID NO:9 and a primer having the base sequence shown in SEQ ID NO:10, and a nucleic acid probe having the base sequence shown in SEQ ID NO:13, that is modified at its 5' terminal by a fluorophore, and that is modified at its 3' terminal by a quencher.

The presence of common wheat in a sample of interest can be qualitatively and/or quantitatively detected, at a high specificity and a high sensitivity, by the common wheat detection method of the present invention. In addition, a very accurate discrimination of whether the wheat in a sample of interest is common wheat, or a non-common wheat such as durum wheat, or both can be carried out with the method of the present invention. The method of the present invention can also quantitatively detect the common wheat and/or non-common wheat, e.g., durum wheat, in a sample of interest.

The method of the present invention is useful as a method for identifying the wheat present in a sample of interest, e.g., in a processed food, and is useful as a method for discriminating among whether this wheat is common wheat, or a non-common wheat (durum wheat is a typical example), or both, and is useful as a method for detecting same.

The method of the present invention can be conveniently, rapidly, and very accurately run using the primer set of the present invention, the nucleic acid probe of the present invention, and the kit of the present invention comprising the preceding.

BEST MODE FOR CARRYING OUT THE INVENTION

Figure 1:
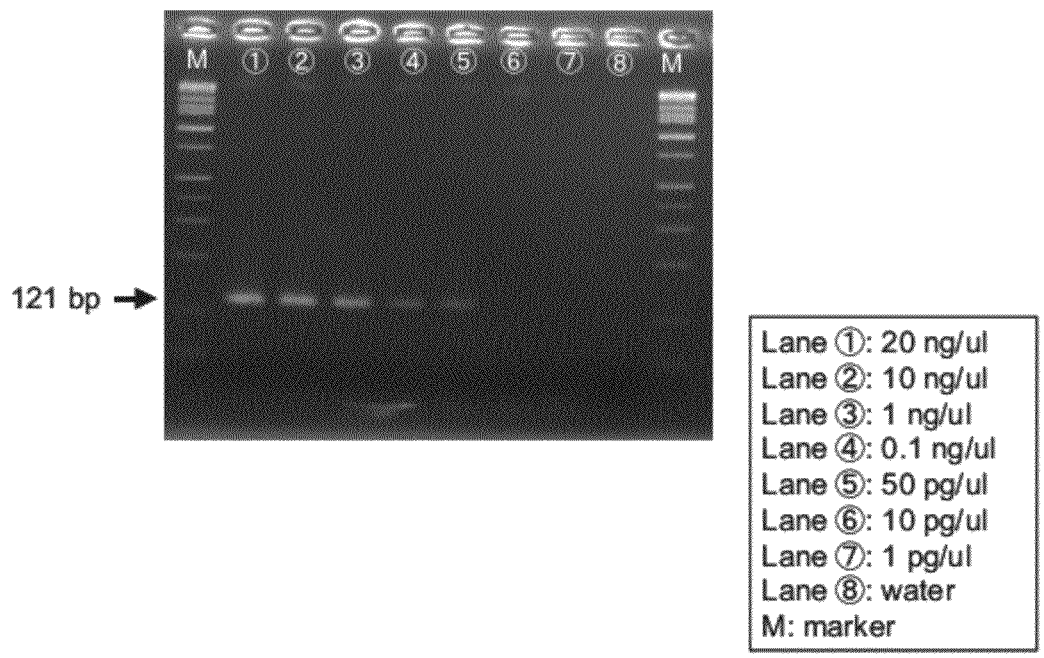
FIG. 1 is a photograph that shows the detection limit for common wheat by PCR.

In the present invention, wheat refers to all wheat cultivated as edible wheat, including common wheats, which have an AABBDD hexaploid genome structure, and two-grain wheats (mainly durum wheat), which are AABB tetraploids. The common wheats can be classified into, for example, the common wheats in general and widespread use as well as club wheat and spelt wheat. In addition to durum wheat, emmer wheat, for example, is also classified as a two-grain wheat.

The present invention is useful for discriminating between common wheat and two-grain wheat, e.g., durum wheat, in various samples of interest, e.g., food raw materials and processed foods.

A detailed description follows for the sample of interest used by the present invention, the extraction of nucleic acid (for example, DNA) from the sample of interest, the preparation of the nucleic acid sample, the target base sequence for detection, the primer set, the nucleic acid probe, the PCR reaction conditions, and the quantitative PCR procedure.

The sample of interest is a sample of interest that permits the extraction of a nucleic acid, e.g., genomic DNA or a fragment thereof, that originates from the sample of interest, but is not otherwise particularly limited. For example, a plant, raw material, material present in a processing step, or a processed food can be used as the sample of interest.

Examples are fresh seeds, dried seeds, powders such as weak wheat flour, semi-processed products such as grits, and foods that have been cooked with heat, such as pastries and noodles. As necessary, these samples of interest can be used processed into a form adapted for extraction of the nucleic acid, for example, by pulverization.

There are no specific boundaries for the wheat content in the sample of interest; however, the presence/absence of wheat in the sample of interest can be discriminated and the presence of wheat can be quantitatively measured in the present invention when the nucleic acid sample solution prepared by extracting nucleic acid from the sample of interest contains at least 10 ppm and preferably not less than 50 ppm wheat-derived nucleic acid.

In addition, in comparison to such biological compounds as proteins, nucleic acid is relatively stable to physical processing, such as the application of heat or pressure, and good detection is possible even when the nucleic acid is present in microamounts in a processed product that has been submitted to such processing.

The preceding means that it will be possible to obtain basic data for detecting a wheat admixture not intended by the manufacturer in various food products.

The nucleic acid originating from the sample of interest preferably is genomic DNA from a plant present in the sample of interest. There are no particular limitations on the method of extracting nucleic acid from the sample of interest, and any method or kit can be used as long as the method secures a quality sufficient for submission to the PCR procedure. For example, the CTAB method can be used or a commercial kit, e.g., a QIAGEN Plant mini Kit (from QIAGEN GmbH), can be used.

These methods can also be modified as necessary. The nucleic acid extracted by these methods is desirably preserved in a state appropriate for use as a template in the PCR procedure; for example, it is preferably dissolved in a suitable buffer and stored at low temperatures. Proceeding in this manner, a nucleic acid solution that will be the nucleic acid sample, for example, a template DNA solution, can be prepared.

The concentration and purity of the obtained nucleic acid can be assayed by measuring the absorbance at 230, 260, 280, and 320 nm using a spectrophotometer. The nucleic acid solution used to carry out the PCR procedure preferably assays as having a 260/230 nm absorbance ratio of at least 2.0 and a 260/280 nm absorbance ratio around 1.8.

Here, there is a risk of RNA admixture as the 260/280 nm ratio approaches 2.0, and because of this caution must be exercised when assaying the DNA concentration.

In order to evaluate the extracted DNA, the development of the PCR reaction may be checked using agarose gel electrophoresis and a primer set complementary to a species-specific gene for the plant constituting the sample of interest.

A large number of genes have been identified as DNA base sequence determination methods have been improved, and to date very large base sequence databases have been widely published by organizations such as the National Center of Biotechnology Information (NCBI) of the National Institutes of Health and the DNA Data Bank of Japan (DDBJ) of the National Institute of Genetics. These databases or a base sequence acquired and analyzed during inhouse experiments may be used for the wheat DNA base sequence that will be the detection target. As a general matter, the DNA of plants, including wheat, is composed of genomic DNA, chloroplast DNA, and mitochondrial DNA. The genomic DNA occurs in the cell as only a single set in the nucleus, while in contrast the chloroplast DNA count and mitochondrial DNA count vary among cells and tissues because they depend on the number of the particular organelle present in a cell.

In order to achieve the objects of the present invention, it was necessary to select, as the detection target, a DNA base sequence that was specific to the DNA in the wheat D genome and for which the copy number in the wheat D genome DNA had been determined. Using the selected base sequence as basic data, a primer set and nucleic acid probe can be designed that are well suited to a PCR-based detection method.

Various conditions are imposed on primer set design. Thus, although any primer set can be used that can specifically amplify the DNA base sequence that is the amplification target, since the genomic DNA in the sample of interest undergoes fragmentation during the processing steps when the sample of interest is a processed food, the primer set is desirably designed to provide a PCR amplification product of 80 to 500 bp and more preferably approximately 80 to 150 bp. In order to obtain a suitable PCR amplification product, the base sequence of the nucleic acid probe used for quantitative PCR and the primer set must satisfy various constraints. The nucleic acid probe used in quantitative PCR is desirably designed to be about 10° C. higher than the Tm value of the corresponding primer set and to have a length of about 18 to 25 bases in order to retain the quenching effect.

The present inventors, taking into account the approaches noted above, discovered a specific base sequence.

Here, the base sequence in SEQ ID NO:5 is the sequence at positions 1769 to 1791 of the wheat SSII-D gene; the base sequence in SEQ ID NO:6 is a sequence complementary to positions 1889 to 1865 of the wheat SSII-D gene; and these form a primer set. In addition, the base sequence in SEQ ID NO:11 is the sequence at positions 1797 to 1819 of the wheat SSII-D gene.

Furthermore, the base sequence in SEQ ID NO:9 is the sequence at positions 3118 to 3136 of the wheat SSII-A gene; the base sequence in SEQ ID NO:10 is a sequence complementary to positions 3231 to 3211 of the wheat SSII-A gene; and these form a primer set. The base sequence in SEQ ID NO:13 is the sequence at positions 3161 to 3185 of the wheat SSII-A gene.

PCR can be carried out using the primer set designed proceeding as above and using nucleic acid extracted from the sample of interest as a template, or quantitative PCR can be carried out using the primer set designed proceeding as above, nucleic acid extracted from the sample of interest as a template, and also a nucleic acid probe.

Execution of the PCR procedure and quantitative PCR procedure can use the usual commercially available equipment and can use various known methods and modifications thereof. There are no particular limitations on the specific procedure used during execution of the PCR procedure or quantitative PCR procedure.

The present invention is directed to a method of detecting the presence of common wheat in a sample of interest, wherein the method comprises carrying out a PCR procedure using a nucleic acid extracted from the sample of interest as a template, a primer having the base sequence shown in SEQ ID NO:5, and a primer having the base sequence shown in SEQ ID NO:6 and detecting the presence of a PCR amplification product.

To carry out the PCR procedure, a PCR reaction solution can be prepared by mixing appropriate amounts of, for example, each of the following reagents: the primer set, the nucleic acid serving as the template, a suitable buffer such as Tris-HCl, dNTP, potassium chloride, magnesium chloride, and a heat-resistant DNA synthetase.

The PCR reaction is composed of the following three steps: thermal denaturation of the template DNA, annealing of the template DNA with the primer set, and a DNA synthesis reaction carried out by the heat-resistant DNA synthetase. Because each of these steps requires different temperatures and times, they are established in suitable ranges considering the base sequence of the region to be amplified and its length. The specific conditions for the steps in the PCR reaction are not particularly limited, and the PCR reaction can be carried out, for example, by holding for 10 minutes at 95° C.; then repeating 35 to 40 cycles where 1 cycle is 30 seconds at 95° C., 30 seconds at 60° C., and 1 minute at 72° C.; holding for 7 minutes at 72° C. after completion of the cycling; and thereafter holding at 4° C.

This reaction can be carried out using the usual commercially available equipment, which also includes equipment for carrying out quantitative PCR.

There are no particular limitations on the detection of the PCR amplification product in the present invention, but detection of the PCR amplification product is typically carried out by an electrophoretic method or a fluorescence detection method. For example, the PCR amplification product from the sample of interest can be subjected to agarose electrophoresis, as necessary in combination with a negative control, a positive control, and a marker, and phoresis is then followed by staining with an intercalator such as ethidium bromide and detection under exposure to ultraviolet light.

In this case, observation of a band for the PCR amplification product then means that common wheat is present in the sample of interest.

The present invention is also directed to a method of qualitatively and/or quantitatively detecting the presence of common wheat in a sample of interest, wherein a quantitative PCR procedure is run using a nucleic acid extracted from the sample of interest as a template and using a primer having the base sequence shown in SEQ ID NO:5, a primer having the base sequence shown in SEQ ID NO:6, and a nucleic acid probe having the base sequence shown in SEQ ID NO:11.

This quantitative PCR procedure generally denotes the execution of a series of reactions in order to quantitate the amount of a template nucleic acid, for example, the amount of a template DNA, in the reaction solution at the start of the PCR amplification reaction. A real-time PCR procedure can specifically be used as the quantitative PCR procedure. An intercalator may be used in the quantitative PCR procedure or a fluorescent-labeled probe may be used. When a fluorescent-labeled probe is used, this probe induces signal variations in correspondence to the number of amplification product molecules produced by the PCR amplification reaction.

The use of a fluorescent-labeled probe is preferred for the present invention, and the use of the TaqMan probe method is more preferred. The nucleic acid probe having SEQ ID NO:11 and the nucleic acid probe having the base sequence of SEQ ID NO:13 can be made into TaqMan probes that can cause the signal variations referenced above. DNA is ordinarily used for this nucleic acid probe.

The previously described nucleic acid probe, double-labeled with a fluorophore and a quencher (a substance that has a quenching activity), is used to carry out the TaqMan probe method. In general, the 5' terminal of the nucleic acid probe is modified with a fluorophore and the 3' terminal is modified with a quencher. The fluorophore can be exemplified by FAM, HEX, TET, and FITC, while the quencher can be exemplified by TAMRA, Eclipse, and DABCYL. There are no particular limitations on the fluorophore and quencher, and use can be made of a suitable selection from fluorophores and quenchers fit for execution of the TaqMan probe method.

Depending on the PCR amplification reaction, the aforementioned TaqMan probe is digested by DNA polymerase and the amount of fluorescence in the PCR reaction solution is increased by the liberation of the fluorophore. An amplification curve is obtained by monitoring the signal intensity detected due to the resulting fluorescence. An increase in fluorescence is then an indicator that expresses the degree of the increase in the PCR amplification product. This makes possible a simple and convenient real-time detection of the status of the amplification during PCR.

To carry out the quantitative PCR procedure, the quantitative PCR procedure is preliminarily carried out on serially diluted standard samples to obtain amplification curves; a threshold cycle (Ct value) is determined by establishing a suitable threshold; a calibration curve is then constructed in advance as a function of the initial amount of template; and the initial amount of template in the sample of interest is determined using this calibration curve. Thus, the Ct value is determined for the sample of interest in the same manner as for the standard samples and the initial amount of template can then be determined by application to the calibration curve.

To carry out the quantitative PCR procedure, a PCR reaction solution can be prepared by mixing appropriate amounts of, for example, each of the following reagents: the primer set, the nucleic acid probe, the nucleic acid serving as the template, a suitable buffer, dNTP, potassium chloride, magnesium chloride, and a heat-resistant DNA synthetase. The reaction conditions for the quantitative PCR procedure can be established in the same manner as described above for the PCR procedure. In addition, known equipment can be used to run the quantitative PCR procedure.

The present invention is further directed to a detection method that combines the previously described method of detecting the presence of common wheat in a sample of interest using a quantitative PCR procedure, with a method of detecting a broad range of wheats using a quantitative PCR procedure.

This is a method of detecting the presence of common wheat and/or a non-common wheat in a sample of interest, and specifically comprises (1) preparing a nucleic acid sample by extracting a nucleic acid from the sample of interest,
  (a) quantitatively detecting the presence of common wheat by implementing a quantitative PCR procedure using this nucleic acid sample, a primer having the base sequence shown in SEQ ID NO:5, a primer having the base sequence shown in SEQ ID NO:6, and a labeled nucleic acid probe having the base sequence shown in SEQ ID NO:11, obtaining an amplification curve by monitoring a signal that corresponds to the amount of amplification product which is generated by this labeled nucleic acid probe, and quantitatively detecting the presence of common wheat using a calibration curve that has been constructed in advance, and
  (b) quantitatively detecting the presence of wheat by implementing a quantitative PCR procedure using the aforementioned nucleic acid sample, a primer having the base sequence shown in SEQ ID NO:9, a primer having the base sequence shown in SEQ ID NO:10, and a labeled nucleic acid probe having the base sequence shown in SEQ ID NO:13, obtaining an amplification curve by monitoring a signal that corresponds to the amount of amplification product which is generated by the labeled nucleic acid probe, and using a calibration curve that has been constructed in advance; and (2) comparing the results of (a) with the results of (b).

For example, the nucleic acid sample prepared by extracting nucleic acid from the sample of interest can be divided in two; for example, it can be divided into at least two equal volumes, and these can be respectively submitted to the quantitative PCR reactions indicated in (a) and (b) above.

For example, the presence of common wheat is confirmed in the preceding method when the presence of common wheat is detected in (a) and its quantitative value does not differ from the quantitative value for wheat in (b). In addition, for example, when the presence of common wheat is detected in (a) and, upon comparing its quantitative value with the quantitative value for wheat in (b), quantitative value in (a)<quantitative value in (b) is found, this difference can be assumed to originate from non-common wheat in the sample of interest and the presence in the sample of interest of both non-common wheat and common wheat can be assumed. Moreover, when, for example, a PCR amplification product is not detected in (a) while a PCR amplification product is detected in (b), this confirms that common wheat is not present in the sample of interest and that a non-common wheat, for example, durum wheat, is present in the sample of interest.

Using this method, the presence of common wheat and wheat in the sample of interest can be quantitatively detected by mathematical calculation using the calibration curves that have been constructed at the same time.

The kit of the present invention can be used as a reagent kit for implementing the PCR procedure or quantitative PCR procedure in the methods of the present invention. The kit of the present invention may also include various optimized reagents for implementing PCR and reagents for detection.

The kit of the present invention, because it can detect trace amounts of wheat and/or common wheat, makes it possible to acquire not only data on whether wheat is present in a sample of interest, but also makes it possible to determine the presence/absence of common wheat and the presence/absence of durum wheat and their respective quantities. As a consequence, a classification can be displayed of the starting wheat flours used in a product that uses durum wheat, e.g., macaroni.

EXAMPLES

The present invention is more specifically described in the examples that follow, but the present invention is not limited to these examples.

1. Method of Constructing a Primer Set for Detecting Common Wheat and a Nucleic Acid Probe for Quantitation <Target Gene Selection>

The genomic DNA of wheat is generally composed of three types of genomes, respectively designated as A, B, and D. Common wheat is a hexaploid having the AABBDD genome, while durum wheat is a tetraploid having the AABB genome. Starch synthase II, which is the target gene for the present invention, is located on the short arm of each chromosome 7 in the wheat A, B, and D genomes; these genes are respectively abbreviated as SSII-A, SSII-B, and SSII-D (Shimbata, T. et al., Mutations in wheat starch synthase II genes and PCR-based selection of a SGP-1 null line. *Theor. Appl. Genet.*, 2005 October; 111(6): 1072-9).

It was concluded that the objects for the present tasks could be achieved if a PCR-based common wheat detection method could be formulated using these genes as the target genes and using a primer set that specifically hybridizes to a base sequence on the D genome, and SSII-D (*Triticum aestivum* wSSII-D gene for starch synthase II-D, complete cds., Accession No. AB201447, total length of 7010 bp) (SEQ ID NO:12) was selected as the detection target gene.

<Design of a Primer Set Specific to SSII-D>

Using the SSII-D gene as the target, a search was performed using the genetic engineering software Primer Express ver. 2.0.0 (from Applied Biosystems Inc.) for base sequences that would be primer candidates. A variety of conditions, e.g., GC content, Tm value, base sequence length, and PCR product length, must be satisfied in order to design an optimal primer. A plurality of primer candidate base sequences were selected as a result. The selected base sequences were narrowed down by a BLAST search to primers that had a high potential for specifically recognizing wheat SSII, and four primer sets were finally selected. The Tm values of these four primer sets were theoretically calculated from the base sequences and were used as an index for establishing the optimal annealing temperature in the PCR reactions. These four primer sets are the SEQ ID NO:1 and SEQ ID NO:2, the SEQ ID NO:3 and SEQ ID NO:4, the SEQ ID NO:5 and SEQ ID NO:6, and the SEQ ID NO:7 and SEQ ID NO:8 shown in Table 2 below.

<Design of an SSII-D-Specific Nucleic Acid Probe for Quantitative PCR>

While several quantitative PCR procedures have already been reported, the TaqMan probe procedure, which is a type of quantitative PCR procedure, was used due to the extensive availability of analytic equipment and reaction reagents. A nucleic acid probe corresponding to each primer set was designed using Primer Express ver. 2.0.0 (from Applied Biosystems Inc.).

With regard to the labeling compounds for the nucleic acid probes, FAM (from Applied Biosystems Inc.) was used for the fluorophore and TAMRA (from Applied Biosystems Inc.) was used for the quencher.

2. Extraction of the Template DNA Used in PCR

Template DNA samples were prepared using seeds from various plants. The plant species are shown in Table 3 below. The surface of the seeds from the wheat, other Poaceae plants, Fabaceae plants, and so forth, was washed with a 1.0% solution of the surfactant SDS followed by thorough rinsing with distilled water and then freeze-drying. These seeds were finely ground using a Multi-Beads Shocker (from Yasui Kikai Corporation) or an ultracentrifugal mill (from Retsch).

The genomic DNA was extracted from each ground sample using a DNA Plant Mini kit (from QIAGEN). The extraction process was carried out using a method taken from the DNA Plant Mini Handbook to which some modifications had been added. Thus, the ground sample was suspended in a mixed solution of AP1 buffer solution and RNase A and Proteinase K and this was held for 2 hours in a reaction layer heated to 37° C. After this, the procedure was carried out according to the Handbook.

For the Proteinase K, 5 µL of a 20 mg/mL Proteinase K solution (from TAKARA BIO INC.) was added per 0.1 g of the ground sample. This quantity of addition can be changed to a more appropriate quantity depending on the type and condition of the seeds.

The extracted DNA was submitted to measurement of the absorbance at 230, 260, 280, and 320 nm using a spectrophotometer in order to determine its purity and concentration and was subjected to 0.8% agarose gel electrophoresis. This was followed by the addition of pure water or TE buffer to dilute to 20 ng/µL to give the template DNA solution for PCR.

3. PCR and Method of Detecting the PCR Amplification Product

AmpliTaq (registered trademark) Gold DNA Polymerase (from Applied Biosystems Inc.) and the reagents provided therewith were used for PCR, and a PCR reaction solution with the following composition was prepared.

Thus, a solution was prepared by thoroughly mixing 2.5 µL PCR buffer II, 2.5 µL 2 mM dNTP mix, 1.5 µL of 25 mM magnesium chloride, 0.125 µL of 5 units/µL AmpliTaq Gold DNA Polymerase, 2 µL of 2.5 µM primer set, and 13.875 µL sterile water, and this was brought to a total of 25 µL by the addition thereto of 2.5 µL of the 20 ng/µL template DNA solution.

A 2720 Thermal Cycler (from Applied Biosystems Inc.) was used for the PCR amplification device, and the reaction conditions shown in Table 1 below were used. The annealing temperature was based on the Tm value for the individual primers as determined by the previously described calculation procedure and was experimentally confirmed in order to establish the optimal temperature for each primer set used in the PCR.

To carry out electrophoresis of the PCR amplification product, appropriate amounts of the PCR reaction solution and a loading buffer were mixed and this was loaded on a 3% agarose gel.

After electrophoresis, ethidium bromide staining was carried out and the presence/absence of common wheat in the sample was assessed by confirming a PCR amplification product of optimal size due to the particular primer set. The validity of the PCR was also checked at this point based on the presence/absence of amplification bands for the negative control and the positive control.

TABLE 1

PCR reaction conditions

| first stage | reaction start | 95° C. | 10 minutes |
|---|---|---|---|
| second stage (40 cycles) | denaturation | 95° C. | 30 seconds |
| | anneal | 55° C., 60° C., or 56° C.* | 30 seconds |
| | extension | 72° C. | 30 seconds |
| third stage | extension | 72° C. | 7 minutes |
| fourth stage | storage | 4° C. | — |

*The annealing temperature varied with the primer set used, and the annealing temperature was set to 55° C. for the set of SEQ ID NO: 1 and SEQ ID NO: 2, the set of SEQ ID NO: 3 and SEQ ID NO: 4, and the set of SEQ ID NO: 7 and SEQ ID NO: 8, to 60° C. for the set of SEQ ID NO: 5 and SEQ ID NO: 6, and to 56° C. for the set of SEQ ID NO: 9 and SEQ ID NO: 10 (refer to Table 2 below).

4. Common Wheat Detection by the Individual Primer Sets

Primer sets 1 to 4, which were designed using the SSII-D (SEQ ID NO:12) encoded in the wheat D genome as the parent sequence, and primer set 5, which was designed using the SSII-A (SEQ ID NO:14) encoded in the wheat A genome as the parent sequence, are shown in Table 2 below.

The base sequence of SEQ ID NO:1 is the sequence at positions 4015 to 4037 of the wheat SSII-D gene; the base sequence of SEQ ID NO:2 is the sequence complementary to positions 4142 to 4122 of the wheat SSII-D gene; the sequence of SEQ ID NO:3 is the sequence at positions 4469 to 4487 of the wheat SSII-D gene; the sequence of SEQ ID NO:4 is the sequence complementary to positions 4555 to 4531 of the wheat SSII-D gene; SEQ ID NO:7 is the sequence at positions 937 to 955 of the wheat SSII-D gene; and SEQ ID NO:8 is the sequence complementary to positions 1080 to 1061 of the wheat SSII-D gene. The sequences in SEQ ID NO:9 and SEQ ID NO:10 correspond, respectively, to the sequences of the SEQ ID NO:3 and SEQ ID NO:4 disclosed in Japanese Patent Application Laid-open No. 2009-5588.

TABLE 2

| primer set | SEQ ID NO | sequence name | base sequence |
|---|---|---|---|
| 1 | 1 | SSII-D4015U | 5'-CAA CAT CCG CAA ATA GTG AGC AT-3' |
| | 2 | SSII-D4142L | 5'-GGC TAG GTC GGG CTC TAT GAG-3' |
| 2 | 3 | SSII-D4469U | 5'-TCC TCG ACC TCC CAT TCC A-3' |
| | 4 | SSII-D4555L | 5'-CCG GTG TTA GTT CTA TGA TGA TTC G-3' |
| 3 | 5 | SSII-D1769U | 5'-CAC CAT CAG TGA AGG AAT GAA TG-3' |
| | 6 | SSII-D1889L | 5'-GGC GAT ATT TGG TAC CTA ATT GAA G-3' |
| 4 | 7 | SSII-D937U | 5'-TCC GTT GTC CCA GCT GAG A-3' |
| | 8 | SSII-D1080L | 5'-TGG CTT TGG AGC TTC TTC GA-3' |
| 5 | 9 | SSII-A3118U | 5'-GGA TGG AAA TCT GGT GTT T-3' |
| | 10 | SSII-A3231L | 5'-ACC ATA ATG GAC CGA GTG TAC-3' |

PCR was performed according to the procedure described above in "3. PCR and method of detecting the PCR amplification product" using these primer sets and template DNA samples obtained as described above from different plants. The results for the presence/absence of a PCR amplification product of optimal size are shown by + and − in Table 3 for each particular primer set.

TABLE 3

| plant species sample | # | plant species production region | primer set 1 | 2 | 3 | 4 | 5 |
|---|---|---|---|---|---|---|---|
| common wheat | 1 | Japan | + | + | + | + | + |
|  | 2 | Japan | + | + | + | + | + |
|  | 3 | United States | + | + | + | + | + |
|  | 4 | Canada | + | + | + | + | + |
|  | 5 | Australia | + | + | + | + | + |
| durum wheat | 6 | Canada | + | + | − | + | + |
|  | 7 | Canada | + | + | − | + | + |
|  | 8 | United States | + | + | − | + | + |
| barley | 9 | Japan | − | − | − | − | − |
|  | 10 | Japan | − | − | − | − | − |
|  | 11 | Japan | − | − | − | − | − |
| rye | 12 | Canada | − | − | − | − | − |
|  | 13 | Germany | − | − | − | − | − |
| buckwheat | 14 | Japan | − | − | − | − | − |
| rice | 15 | Japan | − | − | − | − | − |
| corn | 16 | United States | − | − | − | − | − |
| soybean | 17 | Japan | − | − | − | − | − |

Primer set 3 (SSII-D1769U/1889L: SEQ ID NOS: 5/6) provided a PCR amplification product of the desired length with only the common wheat samples and did not provide a PCR amplification product with any of the other plant species, i.e., durum wheat, barley, rye, buckwheat, rice, corn, and soybean. As a result, this primer set was shown to specifically recognize common wheat.

The other primer sets, on the other hand, also provided a PCR amplification product with the durum wheat samples.

5. Evaluation of the PCR Detection Limit

The semiquantitative detection limit for common wheat DNA was examined by PCR using primer set 3 (SSII-D1769U/1889L: SEQ ID NOS: 5/6), which provided an excellent specific detection of common wheat. Using a salmon sperm DNA solution as the dilution stock, genomic DNA extracted from common wheat was serially diluted to provide 20 ng/μL, 10 ng/μL, 1 ng/μL, 0.1 ng/μL, 50 pg/μL, 10 pg/μL, and 1 pg/μL. PCR was carried out using 2.5 μL of the aforementioned solution as the template DNA solution and using the procedure described above in "3. PCR and method of detecting the PCR amplification product", and 5.0 μL of the PCR solution was subjected to electrophoresis. The detection results are shown in FIG. 1.

The detection limit for primer set 3 using a common wheat DNA solution for the template was 50 pg/μL. This showed that common wheat genomic DNA could be detected using primer set 3 at a high sensitivity of 50 pg/μL by PCR.

6. Confirmation of the Specific Detection of Common Wheat by Quantitative PCR

The ability to specifically detect common wheat in quantitative PCR was investigated using primer set 3 (SSII-D1769U/1889L: SEQ ID NOS: 5/6), which specifically detects common wheat, and a nucleic acid probe in combination therewith.

The DNAs extracted from a total of five samples of interest, i.e., common wheat, durum wheat, barley, rice, and buckwheat, were used as the DNA templates. The validity of the quantitative PCR was confirmed here by the presence/absence of an amplification signal for template DNA-free sterile water as the blank.

A TaqMan Universal PCR Master Mix (from Applied Biosystems Inc.) was used for the quantitative PCR, and a quantitative PCR reaction solution with the following composition was prepared. Thus, a solution was prepared by thoroughly mixing 12.5 μL TaqMan Universal PCR Master Mix (2×), 0.5 μL of 25 μM primer set, 0.5 μL of 10 μM nucleic acid probe, and 9 μL sterile water, and this solution was brought to a total of 25 μl by the addition thereto of 2.5 μL of the template DNA solution. The following were used for the wheat template DNA solution: wheat DNA solutions prepared by the serial dilution, using a salmon sperm DNA solution as the dilution stock, of wheat genomic DNA to provide 20 ng/μL, 10 ng/μL, 1 ng/μL, 0.1 ng/μL, 50 pg/μL, 10 pg/μL, and 1 pg/μL. A DNA solution diluted to 10 ng/μL with a salmon sperm DNA solution was used for the durum wheat, barley, rice, and buckwheat. The nucleic acid probe used in this quantitative PCR is shown in Table 4.

TABLE 4

Sequence of the nucleic acid probe

| SEQ ID NO: | sequence name | base sequence |
|---|---|---|
| 11 | SSII-D-1797T | 5'-TAC CCG ATC GAC CGT TTT GCC CA-3' |

The 5' end of this nucleic acid probe was modified with FAM and its 3' end was modified with TAMRA.

The quantitative PCR reaction was carried out in the present instance using a Rotor-Gene 3000 (from Corbett Research) for the quantitative PCR equipment, but the same results have been obtained using quantitative PCR equipment from other firms.

The reaction conditions were as follows: the reaction solution was held for 10 minutes at 95° C., after which 45 cycles were repeated where 1 cycle was 15 seconds at 95° C. and 30 seconds at 60° C. The amount of fluorescence in each reaction well was continuously measured with elapsed time during the reaction process, and as a result tubes in which there had been an increase in the amount of fluorescence could be determined after the completion of the reaction by analyzing the timewise variation in the amount of fluorescence for each reaction tube. Nucleic acid probe that has hybridized to the target base sequence is degraded during the DNA extension reaction step and, accompanying this, the fluorescent-labeled base is liberated and the amount of fluorescence increases as the PCR amplification reaction progresses. An increase in the amount of fluorescence thus means that a PCR amplification reaction is occurring.

Figure 2:
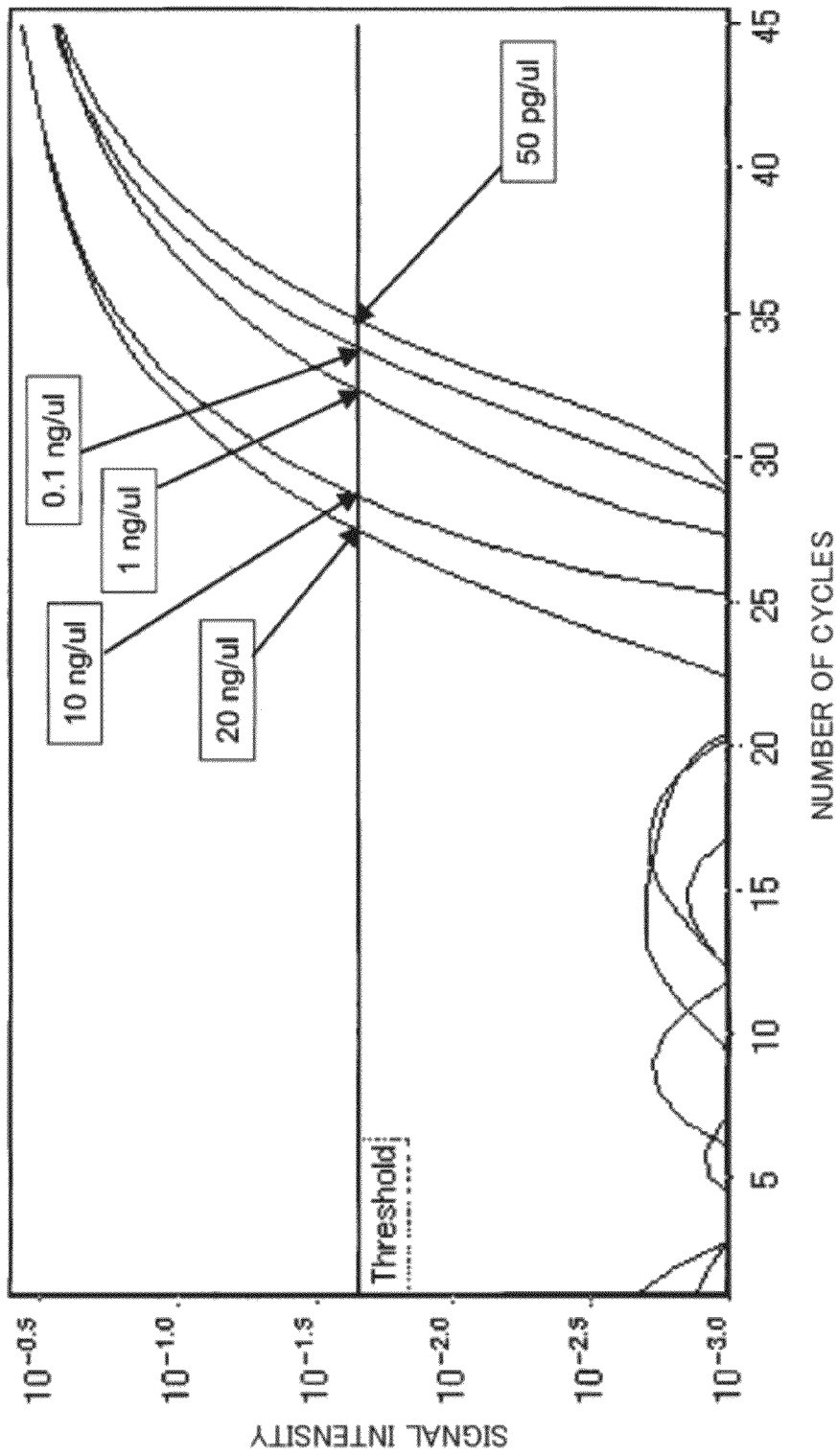
FIG. 2 shows an evaluation (correlation between the number of PCR cycles to reach the threshold line and the logarithm of the template DNA) of primer set 3 (SSII-D1769U/1889L: SEQ ID NOS:5/6) and nucleic acid probe SSII-D1797T (SEQ ID NO:11) for common wheat detection in quantitative PCR.

FIG. 2 gives the results for quantitative PCR carried out using DNA extracted from common wheat for the template. The arrows in the figure indicate the quantitative PCR amplification curves obtained using the different template DNA concentrations. Excellent amplification signals were observed for the combination of primer set 3 with the nucleic acid probe with SEQ ID NO:11, and the detection limit was 50 pg/μL. The number of cycles required for these amplification signals to reach the threshold line resided in a linear relationship with the logarithm of the template DNA concentration, and an entirely suitable quantitative PCR was thus shown to occur.

Figure 3:
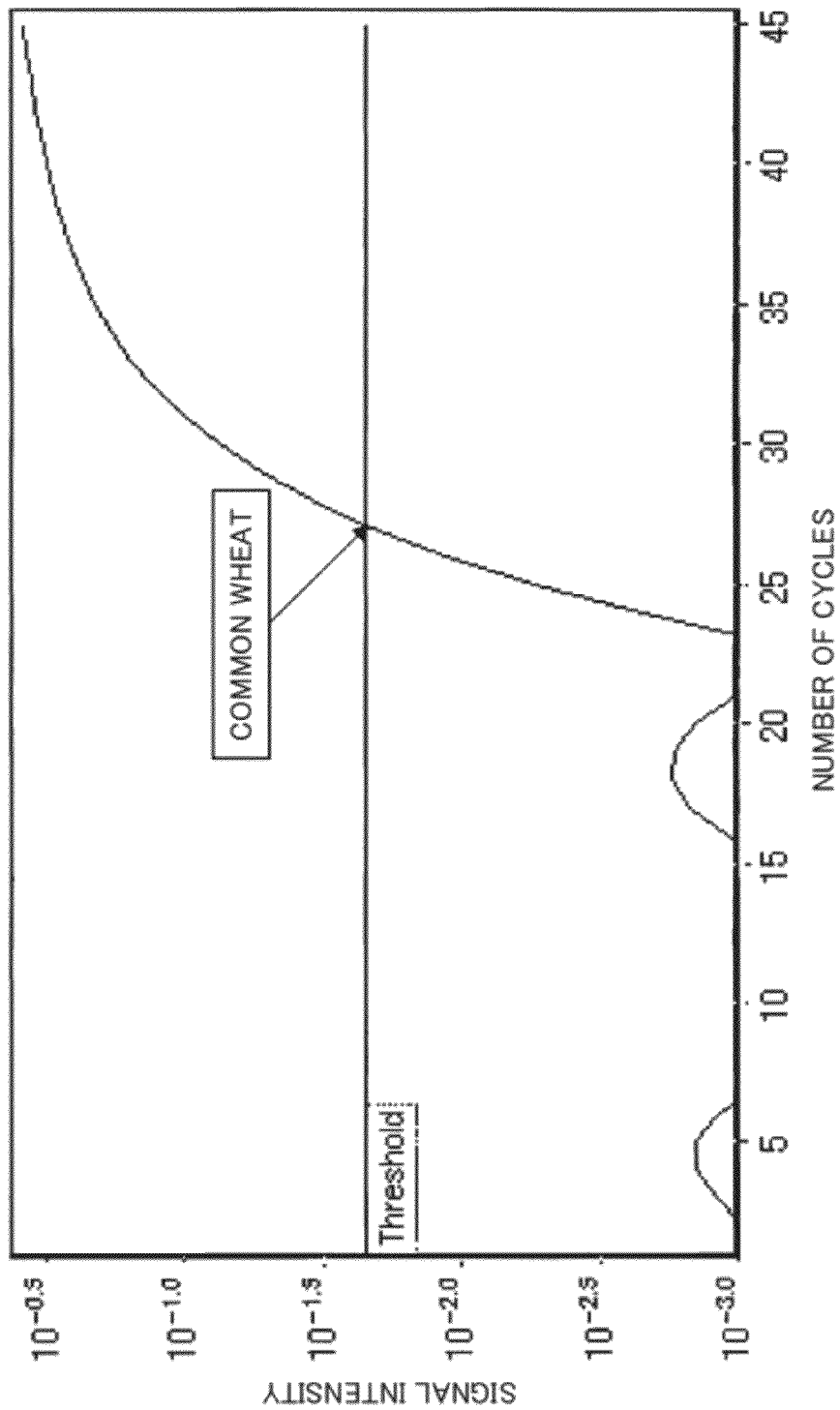
FIG. 3 shows an evaluation (specificity for common wheat of the primer set and nucleic acid probe) of primer set 3 (SSII-D1769U/1889L: SEQ ID NOS:5/6) and nucleic acid probe SSII-D1797T (SEQ ID NO:11) for common wheat detection in quantitative PCR.

In addition, FIG. 3 shows the results of quantitative PCR templated on DNAs extracted from common wheat, durum wheat, barley, rice, and buckwheat. While an amplification signal was obtained for the common wheat, an amplification signal was not obtained for the durum wheat, barley, rice, or buckwheat.

The results in FIGS. 2 and 3 show that the primer set/nucleic acid probe combination indicated above can provide an appropriate and highly sensitive quantitative detection of common wheat.

7. Confirmation of the Specific Detection of Common Wheat and Durum Wheat by the Combination of Two Types of Quantitative PCR It was confirmed whether the common wheat and durum wheat in a sample could each be quantified by carrying out, on the same sample, a quantitative PCR using a primer set that specifically detects wheat DNA and a nucleic acid probe that specifically recognizes that base sequence and a quantitative PCR using a primer set that specifically detects common wheat DNA and a nucleic acid probe that specifically recognizes that base sequence.

For the quantitative PCRs, a quantitative PCR was run according to the previously described procedure using primer set 5 (SSII-A3118U/3231L: SEQ ID NOS:9/10), which specifically detects wheat DNA, and the below-indicated nucleic acid probe SSII-A ex7-T82 corresponding to this primer set, and a quantitative PCR was run according to the previous described procedure using primer set 3 (SSII-D1769U/1889L: SEQ ID NOS:5/6), which specifically detects common wheat DNA, and the nucleic acid probe with SEQ ID NO:11 (SSII-D-1797T).

The following two types of template DNA solutions were prepared as samples.

(1) "Mixed DNA solution samples" prepared by mixing a common wheat genomic DNA solution and a durum wheat genomic DNA solution so as to provide ratios of 100:0, 50:50, 5:95, 0.5:99.5, 0.25:99.75, and 0:100 for the volumetric ratio, with the total DNA concentration being brought to 20 ng/μL.

(2) "Mixed flour samples" prepared by mixing common wheat flour and durum wheat flour so as to provide ratios of 100:0, 50:50, 5:95, 0.5:99.5, 0.25:99.75, and 0:100 for the mass ratio; extracting the genomic DNA therefrom; and adjusting the DNA concentration to 20 ng/μL.

The nucleic acid probe used for quantitation of the wheat DNA is shown in Table 5.

TABLE 5

Sequence of the nucleic acid probe

| SEQ ID NO: | sequence name | base sequence |
|---|---|---|
| 13 | SSII-A ex7-T82 | 5'-CTC CTG CCT GTC TAT CTG AAA GCA T-3' |

The 5' end of this nucleic acid probe was modified with FAM and its 3' end was modified with TAMRA.

Figure 4:
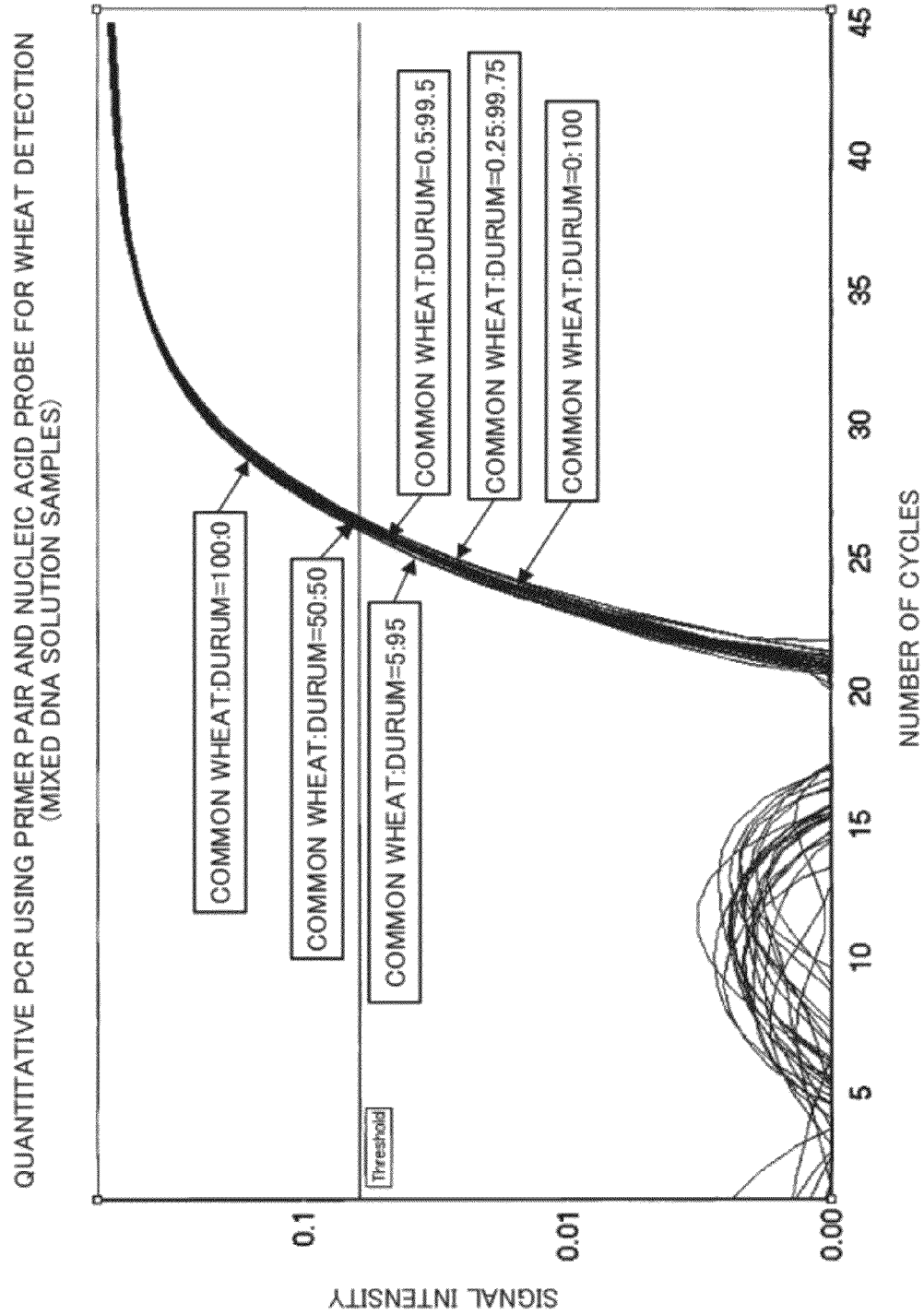
FIG. 4 shows the results of quantitative PCR on mixed solutions of common wheat genomic DNA and durum wheat genomic DNA at different mixing ratios, using primer set 5 (SSII-A3118U/3231L: SEQ ID NOS: 9/10) and nucleic acid probe SSII-A ex7-T82 (SEQ ID NO:13) for wheat detection.
Figure 5:
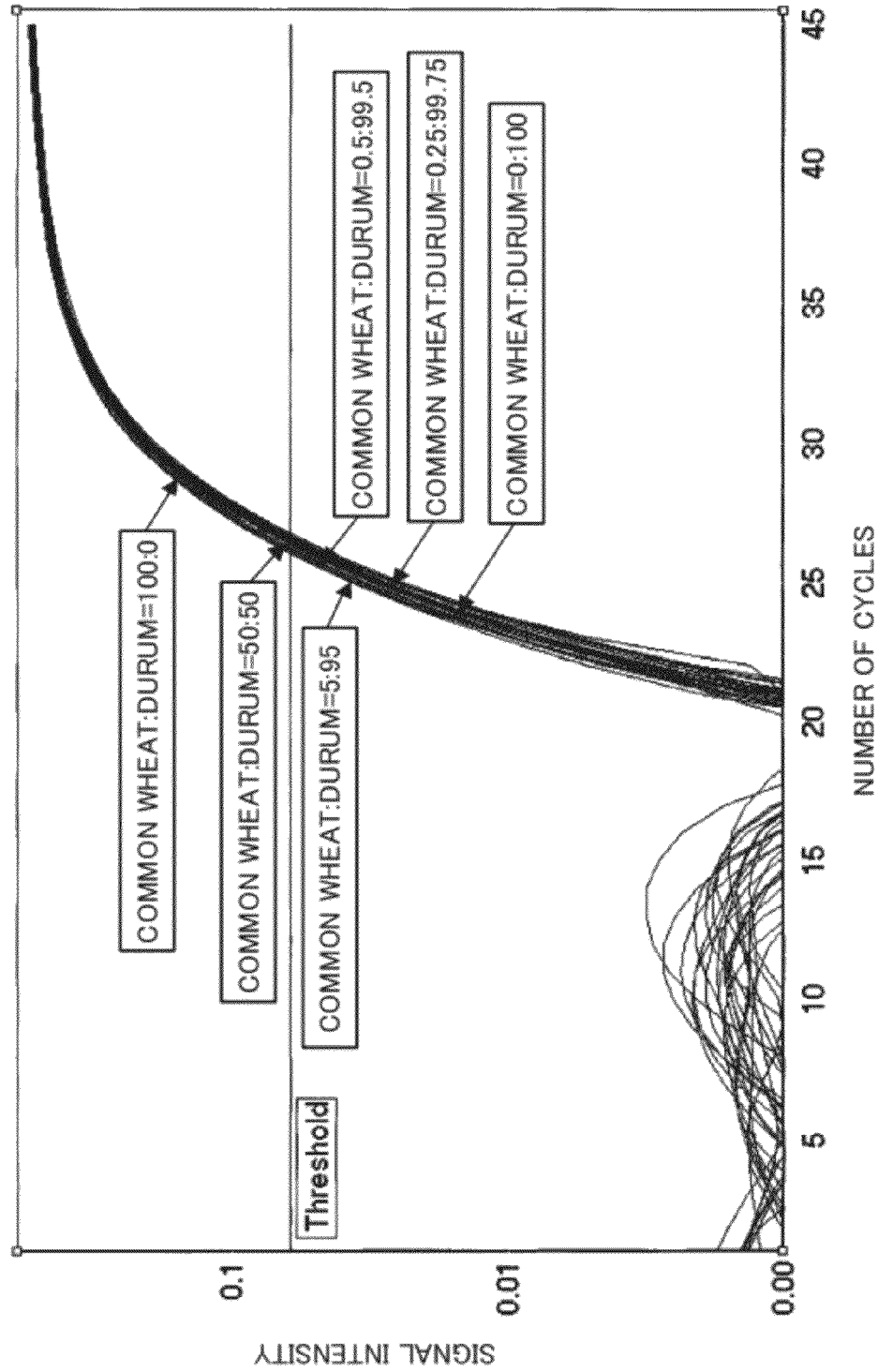
FIG. 5 shows the results of quantitative PCR carried out using primer set 5 (SSII-A3118U/3231L: SEQ ID NOS:9/10) and nucleic acid probe SSII-A ex7-T82 (SEQ ID NO:13) for wheat detection and using template DNAs prepared by extracting the genomic DNA from common wheat flour and durum wheat flour mixed in different proportions.

The results for the quantitative PCR that specifically detects wheat DNA are shown in FIGS. 4 and 5. FIG. 4 shows the results for the use of the "mixed DNA solution samples" as template DNA, while FIG. 5 shows the results for the use of the "mixed flour samples" as template DNA. The arrows in the figures indicate the quantitative PCR amplification curves obtained for the different template DNA concentrations. According to the results in FIGS. 4 and 5, excellent amplification signals were seen for all of the template DNAs using the combination of primer set 5 and the nucleic acid probe with SEQ ID NO:13 and these amplification signals were shown to trace the same curve."

Figure 6:
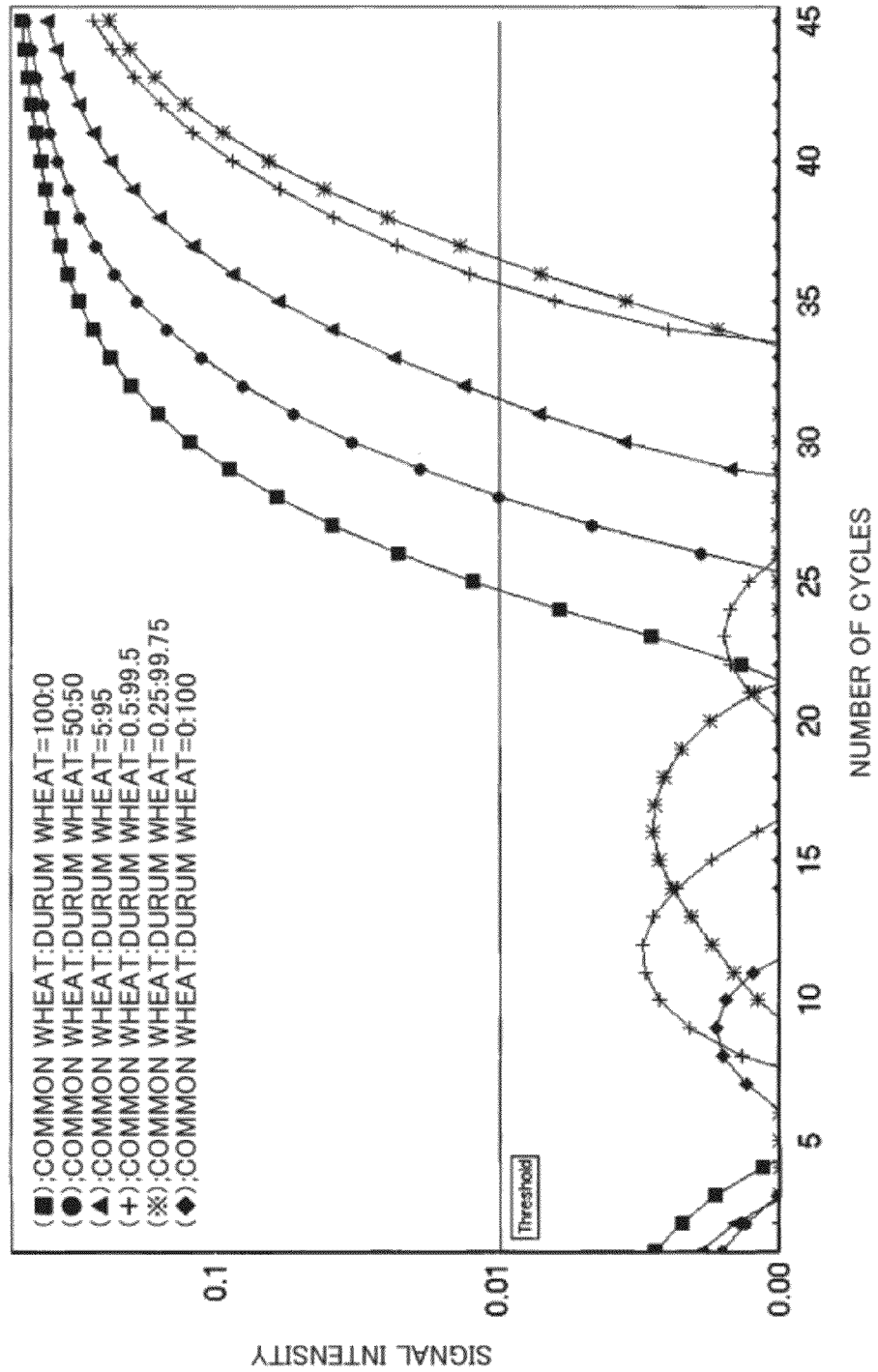
FIG. 6 shows the results of quantitative PCR on mixed solutions of common wheat genomic DNA and durum wheat genomic DNA at different appropriate mixing ratios, using primer set 3 (SSII-D1769U/1889L: SEQ ID NOS: 5/6) and nucleic acid probe SSII-D1797T (SEQ ID NO:11) for common wheat detection.
Figure 7:
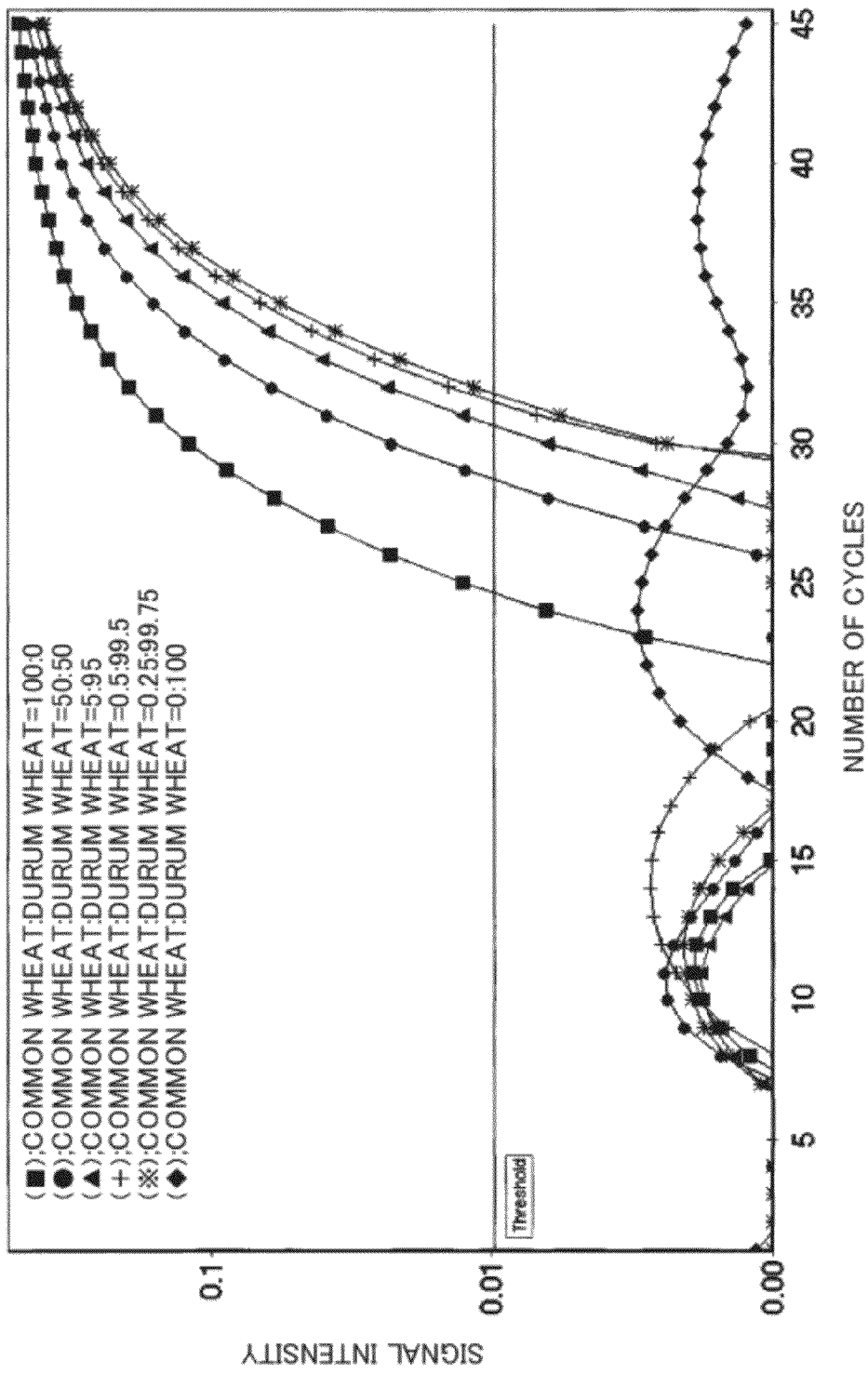
FIG. 7 shows the results of quantitative PCR carried out using primer set 3 (SSII-D1769U/1889L: SEQ ID NOS:5/6) and nucleic acid probe SSII-D1797T (SEQ ID NO:11) for common wheat detection and using template DNAs prepared by extracting the genomic DNA from common wheat flour and durum wheat flour mixed in different appropriate proportions.

The results for the quantitative PCR that specifically detects common wheat DNA are shown in FIGS. 6 and 7. FIG. 6 shows the results for the use of the "mixed DNA solution samples" as template DNA, while FIG. 7 shows the results for the use of the "mixed flour samples" as template DNA. The arrows in the figures indicate the quantitative PCR amplification curves obtained for the different template DNA concentrations. According to the results in FIGS. 6 and 7, excellent amplification signals were observed using the combination of primer set 3 and the nucleic probe with SEQ ID NO:11 for the samples with common wheat:durum wheat mixing ratios of 100:0, 50:50, 5:95, 0.5:99.5, and 0.25:99.75, and it was shown that a sample with a higher common wheat concentration gave a larger amplification signal and resulted in a quicker occurrence of the ascending amplification curve. However, an amplification signal was not obtained for the 0:100 common wheat:durum wheat mixture.

Figure 8:
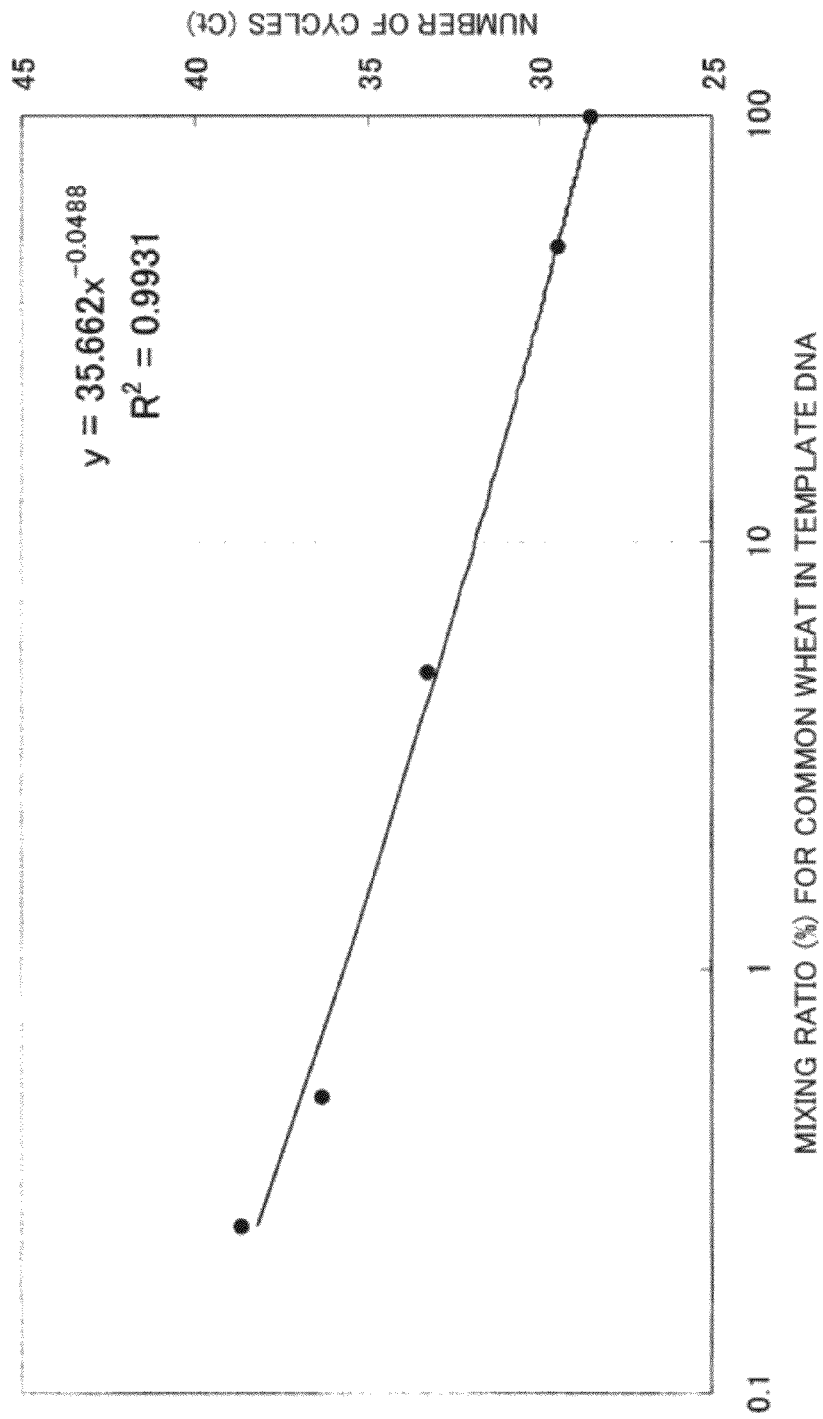
FIG. 8 shows the relationship obtained from the results in FIG. 6 between the common wheat mixing proportion and the number of PCR cycles to reach the threshold line.
Figure 9:
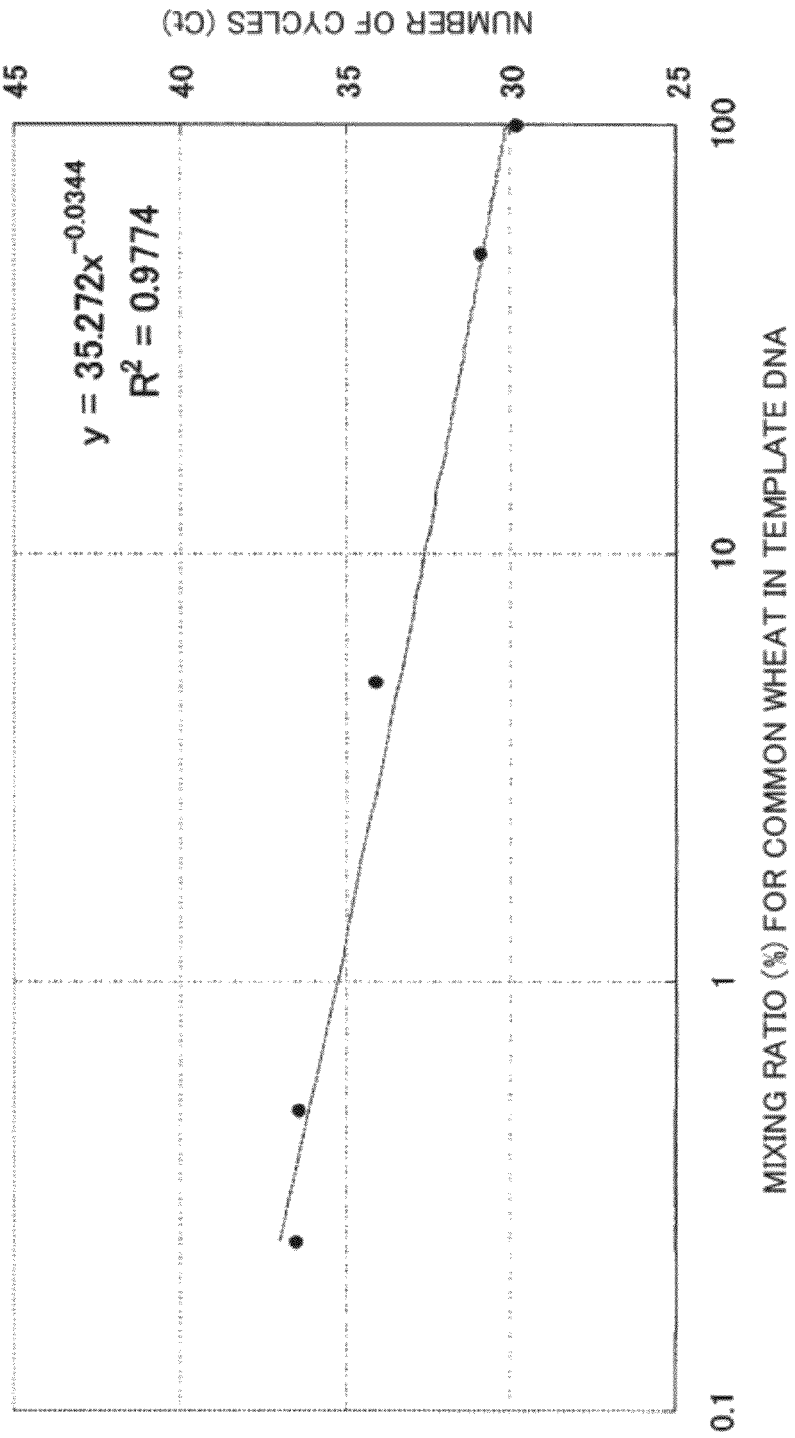
FIG. 9 shows the relationship obtained from the results in FIG. 7 between the common wheat mixing proportion and the number of PCR cycles to reach the threshold line.

Using the results in FIGS. 6 and 7, graphs were prepared, respectively shown in FIGS. 8 and 9, by plotting the common wheat mixing proportion on the horizontal axis and plotting Ct (the threshold cycle, or the number of cycles to reach the threshold line) on the vertical axis. In both FIGS. 8 and 9, it was shown that Ct underwent a proportional decline as the mixing proportion of the common wheat in the template DNA increased and the common wheat could thus be quantitatively determined.

Sequence Listing Free Text
SEQ ID NO:1: PCR primer
SEQ ID NO:2: PCR primer
SEQ ID NO:3: PCR primer
SEQ ID NO:4: PCR primer
SEQ ID NO:5: PCR primer
SEQ ID NO:6: PCR primer
SEQ ID NO:7: PCR primer
SEQ ID NO:8: PCR primer
SEQ ID NO:9: PCR primer
SEQ ID NO:10: PCR primer
SEQ ID NO:11: nucleic acid probe for PCR, modified: 1-FAM-a, 23-a-TAMRA
SEQ ID NO:12: sequence of the wSSII-D gene of *Triticum aestivum*
SEQ ID NO:13: nucleic acid probe for PCR, modified: 1-FAM-a, 25-a-TAMRA
SEQ ID NO:14: sequence of the wSSII-A gene of *Triticum aestivum*

The invention claimed is:

1. A method of detecting the presence of common wheat in a sample of interest, the method comprising: preparing a nucleic acid sample by extracting a nucleic acid from the sample of interest, preforming quantitative PCR procedure using a primer having the base sequence shown by SEQ ID NO: 5 and a primer having the base sequence shown by SEQ ID NO: 6 with the nucleic acid extracted from the sample of interest being used a template; detecting the presence of a PCR amplification product as an indication of common wheat in the sample.

2. A method of qualitatively and/or quantitatively detecting the presence of common what in a sample of interest, the method comprising preparing a nucleic acid sample by extracting a nucleic acid from the sample of interest, performing a quantitative PCR procedure using a primer having the base sequence shown in SEQ ID NO: 5, a primer having the base sequence shown in SEQ ID NO: 6 and a nucleic acid probe having the base sequence shown in SEQ ID NO: 11 with the nucleic acid extracted from the sample of interest being used as template, wherein said nucleic acid probe is labeled, obtaining an amplification curve by monitoring during PCR a signal that corresponds to an amount of an amplification product which is generated by the labeled nucleic acid probe to detect the presence of common wheat in the sample.

3. The method according to claim 2, further comprising quantitatively detecting the presence of common wheat using a calibration curve that has been constructed prior to performing the PCR reaction.

4. A method of detecting the presence of common wheat and/or a wheat other than common wheat in a sample of interest, the method comprising:

(I) preparing a nucleic acid sample by extracting a nucleic acid from the sample of interest, (a) detecting the presence of common wheat by performing a quantitative PCR procedure using the nucleic acid sample, a primer having the base sequence shown in SEQ ID NO:5, a primer having the base sequence shown in SEQ ID NO: 6, and a nucleic acid probe having the base sequence shown in SEQ ID NO: 11 and obtaining an amplification curve by monitoring a signal that corresponds to the amount of an amplification product which is generated by the nucleic acid probe, and (b) detecting the presence of wheat by implementing a quantitative PCR procedure using the nucleic acid sample, a primer having the base sequence shown in SEQ ID NO: 9, a primer having the base sequence shown in SEQ ID NO: 10, and a nucleic acid probe having the base sequence shown in SEQ ID NO: 13 and obtaining an amplification curve by monitoring a signal that corresponds to the amount of an amplification product which is generated by the nucleic acid probe; and (II) comparing the results of (a) with the results of (b).

5. The method according to claim 4, comprising:

(I) in (a), obtaining an amplification curve by monitoring a signal that corresponds to the amount of an amplification product which is generated by the nucleic acid probe and quantitatively detecting the presence of common wheat by using a calibration curve that has been constructed in advance, and in (b), obtaining an amplification curve by monitoring a signal that corresponds to the amount of an amplification product which is generated by the nucleic acid probe and quantitatively detecting the presence of wheat by using a calibration curve that has been constructed in advance; and (II) comparing the quantitative value of (a) with the quantitative value of (b).

6. The method according to claim 4, wherein the nucleic acid probe having the base sequence shown in SEQ ID NO: 11 and the nucleic acid probe having the base sequence shown in SEQ ID NO: 13 are labeled nucleic acid probes.

7. The method according to claim 4, wherein the nucleic acid probe having the base sequence shown in SEQ ID NO: 11 is a nucleic acid probe modified at its 5' terminal by a fluorophore and modified at its 3' terminal by a quencher and the nucleic acid probe having the base sequence shown by SEQ ID NO: 13 is a nucleic acid probe modified at its 5' terminal by a fluorophore and modified at its 3' terminal by a quencher.

* * * * *